(12) United States Patent
Gross et al.

(10) Patent No.: US 7,951,357 B2
(45) Date of Patent: May 31, 2011

(54) IMPLANTABLE POWER SOURCES AND SENSORS

(75) Inventors: Yossi Gross, Moshav Mazor (IL); Ben-Tsion Williger, Kiriat Ono (IL); Tehila Hyman, Modi'in (IL); Tova Neufeld, Ariel (IL)

(73) Assignee: Glusense Ltd., Modi'in (IL)

( * ) Notice: Subject to any disclaimer, the term of this patent is extended or adjusted under 35 U.S.C. 154(b) by 867 days.

(21) Appl. No.: 11/632,587

(22) PCT Filed: Jul. 13, 2005

(86) PCT No.: PCT/IL2005/000743
§ 371 (c)(1),
(2), (4) Date: Nov. 5, 2007

(87) PCT Pub. No.: WO2006/006166
PCT Pub. Date: Jan. 19, 2006

(65) Prior Publication Data
US 2008/0319287 A1 Dec. 25, 2008

Related U.S. Application Data

(60) Provisional application No. 60/588,211, filed on Jul. 14, 2004, provisional application No. 60/658,716, filed on Mar. 3, 2005.

(51) Int. Cl.
*A61B 5/00* (2006.01)
*C07H 21/04* (2006.01)
*C07K 14/00* (2006.01)
*C12N 15/85* (2006.01)

(52) U.S. Cl. ......... 424/9.6; 536/23.4; 530/300; 435/325

(58) Field of Classification Search .................. None
See application file for complete search history.

(56) References Cited

U.S. PATENT DOCUMENTS

| | | |
|---|---|---|
| 3,774,243 A | 11/1973 | Ng et al. |
| 3,837,339 A | 9/1974 | Aisenberg et al. |
| 3,837,922 A | 9/1974 | Ng et al. |
| 3,861,397 A | 1/1975 | Rao et al. |
| 4,140,963 A | 2/1979 | Rao et al. |
| 4,344,438 A | 8/1982 | Schultz |
| 4,352,883 A | 10/1982 | Lim |
| 4,402,694 A | 9/1983 | Ash et al. |
| 4,578,323 A | 3/1986 | Hertl et al. |
| 4,721,677 A | 1/1988 | Clark, Jr. |
| 4,981,779 A | 1/1991 | Wagner |
| 5,001,054 A | 3/1991 | Wagner |
| 5,011,472 A | 4/1991 | Aebischer et al. |
| 5,089,697 A | 2/1992 | Prohaska |
| 5,101,814 A | 4/1992 | Palti |
| 5,116,494 A | 5/1992 | Chick et al. |
| 5,209,231 A | 5/1993 | Cote et al. |
| 5,246,867 A | 9/1993 | Lakowicz et al. |
| 5,368,028 A | 11/1994 | Palti |
| 5,381,075 A | 1/1995 | Jordan |
| 5,427,935 A | 6/1995 | Wang et al. |
| 5,443,508 A | 8/1995 | Giampapa |
| 5,529,066 A | 6/1996 | Palti |
| 5,614,378 A | 3/1997 | Yang et al. |
| 5,626,134 A | 5/1997 | Zuckerman |
| 5,660,940 A | 8/1997 | Larsson et al. |
| 5,702,444 A | 12/1997 | Struthers et al. |
| 5,741,334 A | 4/1998 | Mullon et al. |
| 5,770,454 A | 6/1998 | Essenpreis et al. |
| 5,833,603 A | 11/1998 | Kovacs et al. |
| 5,834,005 A | 11/1998 | Usala |
| 5,855,613 A | 1/1999 | Antanavich et al. |
| 5,879,709 A | 3/1999 | Soon-Shiong et al. |
| 5,902,745 A | 5/1999 | Butler et al. |
| 5,912,005 A | 6/1999 | Lanza et al. |
| 5,998,204 A | 12/1999 | Tsien et al. |
| 6,049,727 A | 4/2000 | Crothall |
| 6,049,728 A | 4/2000 | Chou |
| 6,061,582 A | 5/2000 | Small et al. |
| 6,091,974 A | 7/2000 | Palti |
| 6,163,714 A | 12/2000 | Stanley et al. |
| 6,188,477 B1 | 2/2001 | Pu et al. |
| 6,197,534 B1 | 3/2001 | Lakowicz et al. |

(Continued)

FOREIGN PATENT DOCUMENTS

WO    WO 90/15526    12/1990

(Continued)

OTHER PUBLICATIONS

Bennetto, H.P. et al., (1990) "Electricity generation by microorganisms," National Centre for Biotechnology Education, 1(4): 163-168.
Yamada, K., et al., (2000) "Measurement of Glucose Uptake and Intercellular Calcium Concentration in Single, Living Pancreatic β-Cells," *The Journal of Biological Chemistry*, 275(29): 22278-22283.
Turkewitsch, Petra, et al., (1998) "The Synthesis of Fluorescent Chemosensors Responsive to cAMP and Other Nucleotides," McGill University, Montreal, Quebec.
Gilardi, Gianfrancco, et al., (1997) "Spectroscpic properties of an engineered maltose binding protein," Protein Engineering, 10(5): 479-486.
Hellinga, Homme W. And Marvin, Jonathan S., (1998) "Protein engineering and the development of generic biosensors," TIBTECH, 16(4): 183-189.

(Continued)

*Primary Examiner* — Anand U Desai
(74) *Attorney, Agent, or Firm* — John P. White; Cooper & Dunham LLP

(57) ABSTRACT

A protein is provided, including a glucose binding site, cyan fluorescent protein (CFP), and yellow fluorescent protein (YFP). The protein is configured such that binding of glucose to the glucose binding site causes a reduction in a distance between the CFP and the YFP. Substance monitoring apparatus (210) is also provided, including a semi-permeable barrier (212), adapted to be implanted in a body of a subject and to allow passage therethrough of a substance, while inhibiting passage therethrough of immune cells; and microorganisms (214), disposed within the semi-permeable barrier (212) so as to produce a measurable response to a level of the substance. A sensor (220) is adapted to measure the measurable response and not to measure a response of any mammalian cells that may be disposed within the semi-permeable barrier (212).

19 Claims, 2 Drawing Sheets

U.S. PATENT DOCUMENTS

| | | | |
|---|---|---|---|
| 6,254,601 | B1 | 7/2001 | Burbank et al. |
| 6,294,281 | B1 | 9/2001 | Heller |
| 6,368,592 | B1 | 4/2002 | Colton et al. |
| 6,400,974 | B1 | 6/2002 | Lesho |
| 6,485,703 | B1 | 11/2002 | Coté et al. |
| 6,521,446 | B2 | 2/2003 | Hellinga |
| 6,531,239 | B2 | 3/2003 | Heller |
| 6,577,393 | B1 | 6/2003 | Pötzschke et al. |
| 6,587,704 | B1 | 7/2003 | Fine et al. |
| 6,602,251 | B2 | 8/2003 | Burbank et al. |
| 6,605,039 | B2 | 8/2003 | Houben et al. |
| 6,625,479 | B1 | 9/2003 | Weber et al. |
| 6,630,154 | B1 | 10/2003 | Fraker et al. |
| 6,650,919 | B2 | 11/2003 | Edelberg et al. |
| RE38,525 | E | 6/2004 | Stanley et al. |
| 6,764,488 | B1 | 7/2004 | Burbank et al. |
| 6,846,288 | B2 | 1/2005 | Nagar et al. |
| 6,979,290 | B2 | 12/2005 | Mourlas et al. |
| 7,068,867 | B2 | 6/2006 | Adoram et al. |
| 7,184,810 | B2 | 2/2007 | Caduff et al. |
| 7,223,279 | B2 | 5/2007 | Burbank et al. |
| 2002/0016535 | A1 | 2/2002 | Martin et al. |
| 2002/0072657 | A1 | 6/2002 | Bousquet et al. |
| 2002/0120186 | A1 | 8/2002 | Keimel |
| 2003/0087427 | A1 | 5/2003 | Colton et al. |
| 2003/0117629 | A1 | 6/2003 | Messerschmidt et al. |
| 2003/0134346 | A1 | 7/2003 | Amiss et al. |
| 2003/0216759 | A1 | 11/2003 | Burbank et al. |
| 2003/0232370 | A1 | 12/2003 | Trifiro |
| 2004/0091757 | A1 | 5/2004 | Wang et al. |
| 2004/0109302 | A1 | 6/2004 | Yoneda et al. |
| 2005/0113852 | A1 | 5/2005 | Burbank et al. |
| 2005/0118726 | A1 | 6/2005 | Schultz et al. |
| 2005/0221072 | A1 | 10/2005 | Dubrow et al. |
| 2005/0221276 | A1 | 10/2005 | Rozakis et al. |
| 2007/0004974 | A1 | 1/2007 | Nagar et al. |
| 2007/0066877 | A1 | 3/2007 | Arnold et al. |

FOREIGN PATENT DOCUMENTS

| | | |
|---|---|---|
| WO | WO 91/01680 A1 | 2/1991 |
| WO | WO 91/09312 | 6/1991 |
| WO | WO 96/00106 A1 | 1/1996 |
| WO | WO 98/55869 A1 | 12/1998 |
| WO | WO 01/50983 | 7/2001 |
| WO | WO 03/011445 | 2/2003 |
| WO | WO 03/025220 A3 | 3/2003 |
| WO | WO 2004/028358 A1 | 4/2004 |
| WO | WO 2004/051774 | 6/2004 |
| WO | WO 2004/089465 | 10/2004 |
| WO | WO 2005/053523 A1 | 6/2005 |
| WO | WO 2006/006166 A3 | 1/2006 |
| WO | WO 2006/097933 A3 | 9/2006 |
| WO | WO 2007/110867 A3 | 10/2007 |
| WO | WO 2008/018079 A3 | 2/2008 |

OTHER PUBLICATIONS

Higson, S. P. J. and Vadgama, P. M., (1994) "Biosensors: a viable monitoring technology?" Med. & Biol. Eng. & Comput., 32(6): 601-609.

Tolosa, Leah, et al., (1997) Optical assay for glucose based on the luminescnence decay time of the long wavelength dye Cy5TM, Sensors and Actuators, 45(2): 93-99.

Tolosa, Leah, et al., (1999) "Glucose Sensor for Low-Cost Lifetime-Based Sensing Using a Genetically Engineered Protein," Analytical Biochemistry, 267(1): 114-120.

Marvin, J. S., et al.. (1997) "The rational design of allosteric interactions in a monomeric protein and its applications to the construction of biosensors," *PNAS*, 12(8): 4366-4371.

Pickup, John C., et al., (2005) "Fluorescence-based glucose sensors," Biosensors & Bioelectronics, 20(12): 2555-2565.

Sakurada, Masaya, et al., (1993) "Relation between Glucose-Stimulated Insulin Secretion and Intracellular Calcium Accumulation Studied with a Superfusion System of a Glucose-Responsive Pancreatic β-Cell Line MIN6," *Endocrinology*, 132(6): 2659-2665.

Tolosa, Leah, et al., (1997) "Lifetime-Based Sensing of lucose Using Energy Transfer with a Long Lifetime Donor," Analytical Biochemistry, 250(1): 102-108.

Tsujimura, S., et al., (2001) "Photosynthetic bioelectrochemical cell utilizing cyanobacteria and water-generating oxidase," Enzyme and Microbial Technology 29(4-5): 225-231.

Deuschle, Karen, et al., (2005) "Genetically Encoded Sensors for Metabolites," Cytometry Part A., 64A(1): 3-9.

Serganova, Inna and Blasberg, Ronald, (2005) "Reporter gene imaging: potential impact on therapy," Nuclear Medicine and Biology, 32(7): 763-780.

Laxman, Bharathi, et al., (2002) "Noninvasive real-time imaging of apoptosis," PNAS, 99(26): 16551-16555.

Fehr, Marcus, et al., (2003) "In Vivo Imaging of the Dynamics of Glucose Uptake in Cytosol of COS-7 Cells by Fluorescent Nanosensors," *The Journal of Biological Chemistry*, 278(21): 19127-19133.

Fehr, Marcus, et al., (2004) "Minimally invasive dynamic imaging of ions and metabolites in living cells," Current Opinion in Plant Biology, 7(3): 345-351.

Philippe, H.J., et al., (1997) "Vaginal ligature of uterine arteries during postpartum hemorrhage," International Journal of Gynecology & Obstetrics, 56(3): 267-270.

Pickup, John C., et al., (2004) "In vivo glucose monitoring: the clinical reality and the promise," Biosensors and Bioelectronics, 20(10): 1897-1902.

U.S. Appl. No. 60/820,130, filed Jul. 24, 2006, Gross, et al.

International Search Report issued by the International Searching Authority (ISA/US) on Nov. 23, 2007 in connection with International Application No. PCT/IL07/00399.

International Search Report issued by the International Searching Authority (ISA/US) on Sep. 25, 2008 in connection with International Application No. PCT/IL05/00743.

Ackland-Berglund, C. E., & Leib, D. A. (1995). Efficacy of tetracycline-controlled gene expression is influenced by cell type. *BioTechniques*, 18(2), 196-200.

Amir, O., Cohen, O., Dvir, D., Gabis, E., Monashkin, E., & Karasik, A (2006). *Accurate home and clinical use of a non-invasive continuous glucose monitor*. Abstract submitted for Sixth Diabetes Technology Meeting, Atlanta, GA.

Amir, O., Kononenko, A., Gabis, E., & Karasik, A. (2006) . *Evaluation of a non-invasive continuous glucose monitoring device in a home use setting*. Abstract submitted for 42nd European Association for the Study of Diabetes Annual Meeting, Copenhagen-Malmoe, Denmark-Sweden.

Amir, O., Kononenko, A., Cohen, O., dvir, D., Gabis, E., Monashkin, E., & Karasik, A. (2006). *Highly accurate non-invasive continuous glucose monitoring in clinical and home use settings*, Abstract submitted for America Diabetes Association, 66th Scientific Sessions, Washington, D.C.

Berrebi, A., Amir, O., Weinstein, A., Herzenstein, O., Dvir, D., Monashkin, E., . . . Holland, P. (2006). A non-invasive evaluation of hematocrit with a new optical sensor. *Haematologica*, 91 (s1), 6.

Coté , G. L. (2001). Noninvasive and minimally-invasive optical monitoring technologies. *The Journal of Nutrition*, 131, 1596S-1604S.

Deuschle, K., Okumoto, S., Fehr, M., Looger, L., Kozhukh, L., & Frommer, W. B. (2005). Construction and optimization of a family of genticaly encoded metabolite sensors by semirational protein engineering. *Protein Sci.*, 14, 2304-2314.

Dvir, D., Erlich, S., Singer, J., Fink, T., Kononenko, A., Gabis, E., . . . Singer, P. (2006). *Non invasive blood glucose monitoring in the critically ill patient*. Abstract sumitted for European Society for clinical Nutritiona nd Metabolism 28th ESPEN Congress, Istanbul.

Fillat, C., Carrió, M., Cascante, A., & Sangro B. (Feb. 2003), Suicide gene therapy mediated by the herpes simplex virus thymidine kinase gene/ganciclovir system: fifteen years of application. *Current Gene Therapy*, 3(1), 13-26.

Klueh, U., Dorsky, D. I., & Kreutzer, D. L. (Jun. 7, 2004). Enhancement of implantable glucose sensor function in vivo using gene transer-induced neovascularization. *Biomaterials*, 26(10), 1155-1163.

Kononenko, A., Dvir, D., Grunberg, B., Cohen, J., Gabis, E., & Singer, P. (Mar. 21, 2006). *Evaluation of a noninvasive blood glucose monitoring device for critically ill patients*. Abstract submitted for 26th International Symposium on Intensive Care and Emergency Medicine, Brussels, Belgium.

Koo, T., Berger, A. J., Itzkan, I., Horowitz, G., & Feld, M. S. (Apr. 1998). Measurement of glucose in human blood serum using Raman spectroscopy. *IEEE LEOS Newsletter*, 12(2), 18.

Liu, L., & Sheardown, H. (2004). Glucose permeable poly (dimethyl siloxane) poly (N-isopropyl acrylamide) interpenetrating networks as ophthalmic biomaterials. *Biomaterials*, 26(3), 233-244.

Lo, Y., & Yu, T. (2005). A polarimetric glucose sensor using a liquid-crystal polarization modulator driven by a sinusoidal signal. *Optics Communications*, 259(1), 40-48.

McNichols, R. J., Cameron, B. D., & Coté, G. L. (Apr. 1998). Development of a non-invasive polarimetric glucose sensor. *IEEE LEOS Newsletter*, 12(2), 30-31.

Moschou, E. A., Sharma, B. V., Deo, S. K., & Daunert, S. (Sep. 2004). Fluorescence glucose detection: advances toward the ideal in vivo biosensor. *Journal of Fluorescence*, 14(5), 535-547.

Olesberg, J. T. (2001). Noninvasive blood glucose monitoring in the 2.0-2.5 μm wavelength range. *The 14th Annual Meeting of the IEEE Lasers and Electro-Optics Society*, 2, 529.

Olesberg, J. T., Arnold, M. A., Mermelstein, C., Schmitz, J., & Wagner, J. (2005). Tunable laser diode system for noninvasive blood glucose measurements. *Appl. Spectrosc.*, 59(121), 1480-1484.

Olesberg, J. T., Liu, L., Zee, V. V., & Arnold, M. A. (Nov. 30, 2005). In vivo near-infrared spectroscopy of rat skin tissue with varying blood glucose levels. *Anal. Chem.*, 78(1), 215-223.

Olesberg, J. T., Cao, C., Yager, J. R., Prineas, J. P., Coretsopoulos, C., Arnold, M. A., . . . Santilli, M. (2006). Optical microsensor for continous glucose measurements in interstitial fluid. *Optical Diagnostics and Sensing VI, Proc. Of SPIE*, 6094, 609403-1-609403-10.

Patounakis, G., Shepard, K. L., & Levicky, R. (Nov. 2006). Active CMOS array sensor for time-resolved fluorescence detection. *IEEE Journal of Solid-State Circuits*, 41(11), 2521-2530.

Primack, H. (2006). *Non-invasive optical sensing of blood hemoglobin and glucose*. Abstract submitted for Photonics West 2006, San Jose, CA.

Primack, H. (2006). *Non-invasive sensing of glucose and hemoglobin*. Abstract submitted for Optical Imaging 2006, Bethesda, MD.

Reszka, R., Jacobs, A., & Voges, J. (2005). Liposome-mediated suicide gene therapy in humans. *Methods in Enzymology*, 391, 200-208.

Scognamiglio, V., Staiano, M., Rossi, M., & D'Auria, S. (Sep. 2004,). Protein-based biosensors for diabetic patients. *Journal of Fluorescence*, 14(5), 491-498.

Wan, Q. (Dec. 2004,). Dual wavelength polarimetry for monitoring glucose in the presence of varying birefringence (Thesis, Office of Graduate Studies of Texas A&M University, 2004).

Ye, K., & Schultz, J. S. (Jun. 6, 2003,). Genetic engineering of an allosterically based glucose indicator protein for continuous glucose monitoring by fluorescence resonance energy transfer. *Anal. Chem.*, 75(14), 3451-3459.

Yokota, M., Sato, Y., Yamaguchi, I., Kenmochi, T., & Yoshino, T. (2004). A compact polarimetric glucose sensor using a high-performance fibre-optic Faraday rotator. *Meas. Sci. Technol.*, 15, 143-147.

Yonzon, C. R., Haynes, C. L., Zhang, X., Walsh, J. T., & Van Duyne, R. P. (Nov. 25, 2003). A glucose biosensor based on surface-enhanced Raman scattering: improved partition layer, temporal stability, reversibility, and resistance to serum protein interference. *Anal. Chem.*, 76(1), 78-85.

Notification of Transmittal of the International Search Report and the Written Opinion of the International Searching Authority, Or the Declaration, including an International Search Report and Written Opinion, mailed Apr. 30, 2010 in connection with PCT International Application No. PCT/IL09/01214, filed Dec. 24, 2009.

Communication forwarding an Extended European Search Report, including a Supplementary European Search Report and European Search Opinion, issued Dec. 16, 2009 in connection with European Patent Application No. 05758905.3.

Communication forwarding a new European Search Report, including a Supplementary Partial European Search Report and European Search Opinion, issued Feb. 4, 2010 in connection with European Patent Application No. 07736139.2.

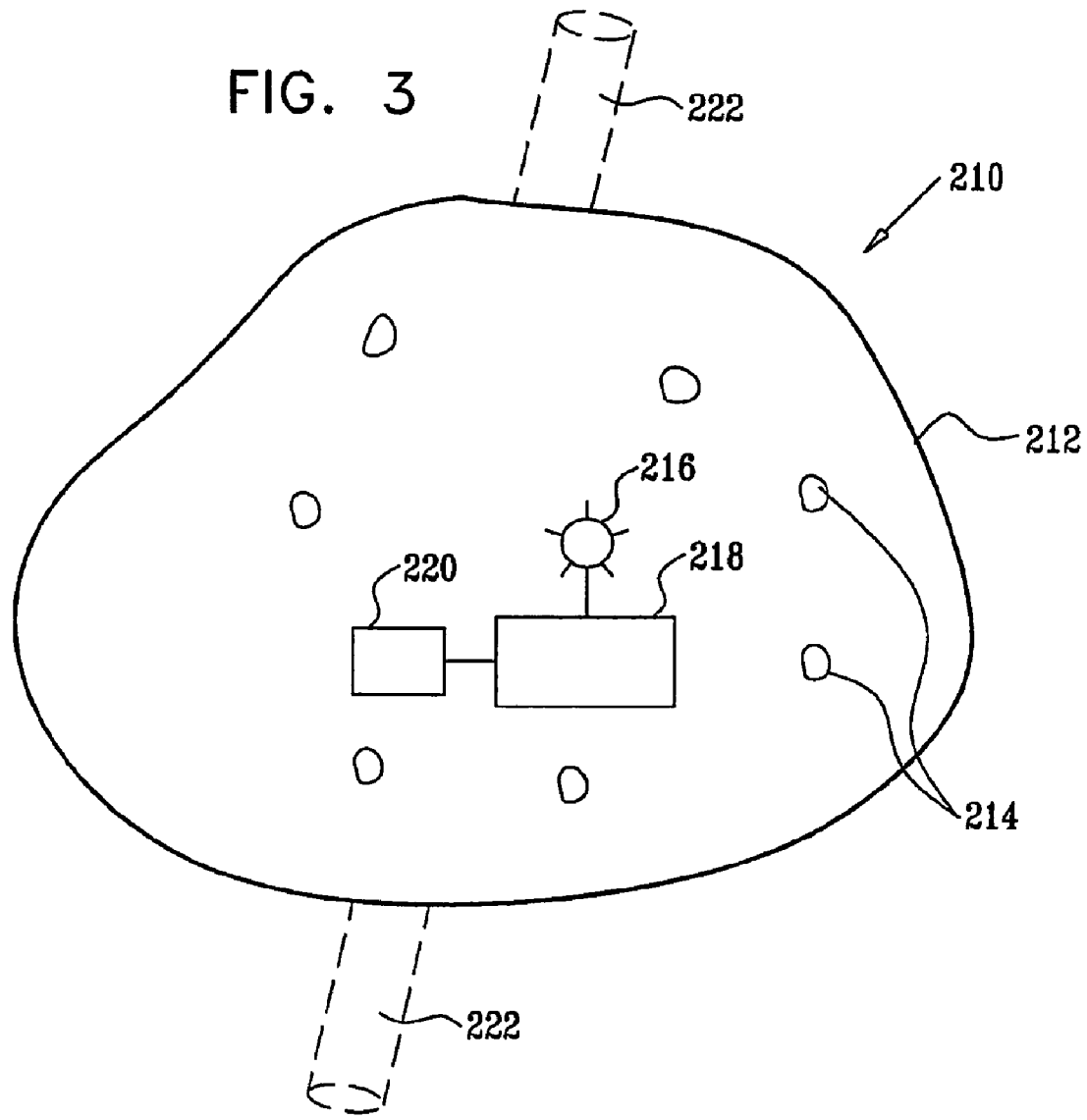

IMPLANTABLE POWER SOURCES AND SENSORS

CROSS-REFERENCES TO RELATED APPLICATIONS

This application is a §371 national stage of PCT International Application No. PCT/IL2005/000743, filed Jul. 13, 2005, and claims the benefit of U.S. Provisional Applications Nos. 60/658,716, filed Mar. 3, 2005; and 60/588,211, filed Jul. 14, 2004, the contents of all of which are hereby incorporated by reference into this application.

REFERENCE TO SEQUENCE LISTING

This application incorporates-by-reference nucleotide and/or amino acid sequences which are present in the file named "110418_0518_77411_Substitute_Sequence_Listing_GC.txt," which is 24.2 kilobytes in size, and which was created Apr. 18, 2011 in the IBM-PC machine format, having an operating system compatibility with MS-Windows, which is contained in the text file filed Apr. 18, 2011 as part of this application.

FIELD OF THE INVENTION

The present invention relates generally to implantable power sources and sensors, and specifically to implantable bio-fuel cells and methods and apparatus for sensing blood glucose concentrations.

BACKGROUND OF THE INVENTION

Fluorescence resonance energy transfer (FRET) is the transfer of photon energy from an excited fluorophore (the donor) to another fluorophore (the acceptor) without the emission of a photon, when the donor and acceptor molecules are in close proximity to each other. FRET enables the determination of the relative proximity of the molecules, for investigating, for example, molecular interactions between two protein partners, structural changes within one molecule, and ion concentrations. Fluorescent proteins (FPs) can be genetically fused to proteins of interest and expressed in cells. FP pairs useful for performing FRET measurements in living cells include cyan fluorescent protein (CFP) as the donor, and yellow fluorescent protein (YFP) as the acceptor, because the emission spectrum of CFP partially overlaps the excitation spectrum of YFP.

U.S. Pat. No. 3,837,339 to Aisenberg et al., which is incorporated herein by reference, describes techniques for monitoring blood glucose levels, including an implantable glucose diffusion-limited fuel cell. The output current of the fuel cell is proportional to the glucose concentration of the body fluid electrolyte and is therefore directly indicative of the blood glucose level. This information is telemetered to an external receiver which generates an alarm signal whenever the fuel cell output current exceeds or falls below a predetermined current magnitude which represents a normal blood glucose level. Valve means are actuated in response to the telemetered information to supply glucose or insulin to the monitored living body.

U.S. Pat. No. 3,861,397 to Rao et al., which is incorporated herein by reference, describes an implantable fuel cell that uses an oxidizable body substance, preferably glucose, as well as oxygen from the body fluids.

U.S. Pat. No. 4,140,963 to Rao et al., which is incorporated herein by reference, describes a device for measuring blood sugar levels, including an electrochemical glucose cell that produces an electrical signal corresponding to the sugar concentration. The glucose cell produces in conjunction with a sugar solution (as electrolyte) an electrical signal which represents a measure of the present sugar concentration value. The cell can be operated, for example, by an outer source of current, a battery, or a fuel cell, for example a glucose-oxygen cell. The cell itself can also provide its own current; it may be constructed, for example, as a glucose-oxygen-fuel cell or as a glucose/silver/silver-chloride cell.

U.S. Pat. No. 3,837,922 to Ng et al., which is incorporated herein by reference, describes an implantable fuel cell power source for an artificial heart or pacemaker device which utilizes blood carbohydrates as the anode fuel. The cathode of the implantable fuel cell is an oxygen utilizing cathode, and may be air breathing, for example, following being ventilated through a percutaneous airway by a balloon system. The anode is separated from the whole venous blood by a thin, porous membrane capable of passing a blood ultra-filtrate containing the oxidizable organics.

U.S. Pat. No. 3,774,243 to Ng et al., which is incorporated herein by reference, describes an implantable hybrid power system for artificial hearts or pacemakers, which includes a fuel cell assembly air-breathing cathode assembly. A storage battery is combined with a fuel cell for peak power requirements and for more nearly steady-state fuel cell operation. The fuel cell may have either an external anode fuel source, such as hydrogen or hydrazine, or utilize blood carbohydrates, such as glucose. Electrical output from the power system is used to power any desired type of artificial heart or pacemaker device.

U.S. Pat. No. 6,294,281 and US Patent Application Publication 2002/0025469 to Heller, which are incorporated herein by reference, describe a fuel cell having an anode and a cathode, with an anode enzyme disposed on the anode and a cathode enzyme disposed on the cathode. The fuel cell typically uses as fuel compounds available in a biological system. The fuel for the operation of the fuel cell may be provided by compounds in blood, sap, and other biological fluids or solids. Such compounds may include, for example, sugars, alcohols, carboxylic acids, carbohydrates, starches, cellulose, and dissolved or complexed oxygen (e.g., oxygen complexed with a biomolecule such as hemoglobin or myoglobin). Examples of compounds for electroreduction or electrooxidation in the operation of a fuel cell in an animal include glucose or lactate at the anode and oxygen, dissolved as molecular oxygen or bound in hemoglobin or myoglobin, at the cathode.

US Patent Application Publication 2004/0091757 to Wang et al., which is incorporated herein by reference, describes an implantable fuel cell assembly containing a device for converting fat to glycerol and fatty acid, a device for converting glycerol to hydrogen, a device for converting fatty acid to hydrogen, a device for converting a bodily fluid to a gas selected from the group consisting of hydrogen, oxygen, and mixtures thereof, and a fuel cell for producing electricity from hydrogen and oxygen.

U.S. Pat. No. 5,660,940 to Larsson et al., which is incorporated herein by reference, describes a method for producing electric energy in a biofuel-powered fuel cell, the metal in the first acid metallic salt solution forming a redox pair having a normal potential between −0.1 and 0.7 V and the metal in the second acid metallic salt solution forming a redox pair having a normal potential between 0.7 and 1.3 V, both metals preferably being vanadium which forms the redox pairs vanadium (IV)/(III) and vanadium (V)/(IV), respectively.

U.S. Pat. No. 4,578,323 to Hertl et al., which is incorporated herein by reference, describes a fuel cell which produces electricity from the anaerobic oxidation of hydroxylic compounds, e.g. alcohols and sugars, in the presence of a quinone. For applications in which the fuel used has a greater affinity for its electrons than the quinone compound in its ground state, the oxidation half cell mixture must be irradiated with light energy.

U.S. Pat. Nos. 5,368,028 and 5,101,814 to Palti, which are incorporated herein by reference, describe methods and apparatus for monitoring blood glucose levels by implanting glucose sensitive living cells, which are enclosed in a membrane permeable to glucose but impermeable to immune system cells, inside a patient. Cells that produce detectable electrical activity in response to changes in blood glucose levels are used in the apparatus along with sensors for detecting the electrical signals, as a means for detecting blood glucose levels. Human beta cells from the islets of Langerhans of the pancreas, sensor cells in taste buds, and alpha cells from the pancreas are discussed as appropriate glucose sensitive cells.

U.S. Pat. Nos. 6,091,974 and 5,529,066 to Palti, which are incorporated herein by reference, describe a capsule for encapsulating implantable cells for improving the detectability of electrical signals generated by the cells. The capsule includes a low-conductivity (high electrical resistance) membrane and a semi-permeable (low electrical resistance) membrane. The low-conductivity membrane seals around the circumference of the cell mass between the electrical poles of the capsule, and further extends for increasing the electrical resistance between the poles. The semi-permeable membrane enables nutrients and waste materials to flow to and from the cell mass. The semi-permeable membrane encloses at least one of the poles of the cell mass, and cooperates with the low-conductivity membrane to completely enclose the cell mass. The low-conductivity membrane may enclose one of the poles, if desired. Electrodes are used to detect the electrical signals from the cell mass.

US Patent Application 2002/0038083 to Houben and Larik, which is incorporated herein by reference, describes methods and apparatus for monitoring blood glucose levels by implanting glucose sensitive living cells, which are enclosed in a membrane permeable to glucose but impermeable to immune system cells, inside a patient. The living cells come from the islets of Langerhans of the pancreas and have been genetically engineered so as to grow on a substrate containing interdigitated electrodes, which serves as a sensor of cellular electrical activity.

U.S. Pat. No. 6,605,039 to Houben and Larik, which is incorporated herein by reference, describes methods and apparatus for monitoring blood glucose levels by implanting glucose sensitive living cells, which are enclosed in a membrane permeable to glucose but impermeable to immune system cells, inside a patient. The heat response of cells from the islets of Langerhans of the pancreas to glucose levels is proposed as a glucose sensor along with measurements of the membrane impedance of pancreatic B-cells as a result of glucose exposure.

U.S. Pat. No. 6,650,919 to Edelberg and Christini, which is incorporated herein by reference, describes methods and apparatus for monitoring physiological or pathophysiological variables in a living organism by implanting tissue or cells capable of carrying out physiological or pathophysiological functions. Particular applications involving the use of cardiac or neuronal tissue to monitor cardiac function and health are discussed.

U.S. Pat. No. 6,368,592 to Colton et al., which is incorporated herein by reference, describes techniques for supplying oxygen to cells in vitro or in vivo by generating oxygen with an oxygen generator that electrolyzes water to oxygen and hydrogen. The oxygen generator may be used to supply oxygen to cells contained in an encapsulating chamber for implanting in the body such as an immunoisolation chamber bounded by a semipermeable barrier layer that allows selected components to enter and leave the chamber. A bioactive molecule may be present with the cells. US Patent Application Publication 2003/0087427 to Colton et al., which is incorporated herein by reference, describes similar techniques.

U.S. Pat. No. 5,443,508 to Giampapa, which is incorporated herein by reference, describes an implantable biological agent delivery system. The system includes a pod adapted for subcutaneous implantation beneath the dermis of the skin. The pod includes a porous surface and has at least one internal chamber which is in fluid communication with the porous surface. The system includes a dome adapted to be detachably secured to the chamber. The dome includes interior chambers, each in fluid communication with the interior of the pod. Prior to implantation, the chambers are loaded with bioactive agents, such as hormones, enzymes, biologic response modifiers, free radical scavengers, or genetically altered cell cultures. Time-release micropumps pump the agents into the interior chambers of the pod for transmission through the porous surfaces into a growth factor-stimulated capillary matrix and then to the bloodstream of the subject. The pod may be removed, refilled, and resecured to the dome upon exhaustion of its contents or upon medical requirement for changes in medication, or may be percutaneously refilled in situ through injection into the dome. The surface of the pod may be treated with one or more vascular growth factors or related biologic molecules.

U.S. Pat. No. 5,614,378 to Yang et al., which is incorporated herein by reference, describes a photobioreactor system for oxygen production for a closed ecological life support system. The photobioreactor is described, among other things, as being useful for converting carbon dioxide to oxygen in an artificial lung.

U.S. Pat. No. 4,721,677 to Clark, Jr., which is incorporated herein by reference, describes an implantable biosensor and method for sensing products, such as hydrogen peroxide, generated from an enzymatic reaction between an analyte, like glucose, and an enzyme in the presence of oxygen. The biosensor is equipped with an enclosed chamber for containing oxygen and can be adapted for extracting oxygen from animal tissue adjacent the container. The biosensor is designed to optically or electrically sense products generated from the enzymatic reaction which serve as a function of the analyte.

U.S. Pat. No. 5,855,613 to Antanavich et al., which is incorporated herein by reference, describes embedding cells in a thin sheet of alginate gel that is then implanted in a body.

U.S. Pat. No. 5,834,005 to Usala, which is incorporated herein by reference, describes immunoisolating cells by placing them in a chamber that is implanted inside the body. In the chamber, the cells are shielded from the immune system by means of a membrane permeable to small molecules such as glucose, oxygen, and the hormone secreted by the cells, but impermeable to cells and antibodies.

U.S. Pat. No. 4,402,694 to Ash et al., which is incorporated herein by reference, describes a body cavity access device for supplying a hormone to a patient. The device includes an implantable housing placed in the body and having an impermeable extracorporeal segment and a semipermeable subcutaneous segment. A hormone source such as live, hormone-producing cells, e.g., pancreatic islet cells, is then removably positioned in the housing to provide a hormone supply to the patient. A sensor can be located within the subcutaneous segment and operably associated with a dispenser to release medication into the housing and to the patient.

U.S. Pat. No. 5,011,472 to Aebischer et al., which is incorporated herein by reference, describes techniques for providing hybrid, modular systems for the constitutive delivery of active factor to a subject and, in some instances, to specific anatomical regions of the subject. The systems include a cell reservoir containing living cells capable of secreting an active agent, which is preferably adapted for implantation within the body of the subject and further includes at least one semipermeable membrane, whereby the transplanted cells can be nourished by nutrients transported across the membrane while at the same time protected from immunological, bacterial, and viral assault. The systems further include a pumping means, which can be implantable or extracorporeal, for drawing a body fluid from the subject into the cell reservoir and for actively transporting the secreted biological factors from the cell reservoir to a selected region of the subject.

U.S. Pat. No. 5,116,494 to Chick et al., which is incorporated herein by reference, describes a device that serves as an artificial pancreas. The device comprises a hollow fiber which is surrounded by islets of Langerhans enclosed in a housing. The islets are suspended in a temperature sensitive matrix which is sufficiently viscous to support islets at a temperature below about 45 degrees C. and sufficiently fluid to enable removal of islet suspension at a temperature above about 45 degrees C. A warm (e.g., 48 degree to 50 degree C. solution) may be flushed through the device to change the physical state of the temperature sensitive matrix from a semi-solid state to a liquefied semi-gel state. The temperature sensitive supporting material is described as enabling long-term maintenance of islet cells in in vitro culture.

U.S. Pat. No. 5,741,334 to Mullon et al., which is incorporated herein by reference, describes an artificial pancreatic perfusion device comprising a hollow fiber having a porosity ranging from about 25 Kd to about 200 Kd. The hollow fiber has one end connected to a blood vessel for receiving blood and a second end connected to a blood vessel for returning the blood. Islets of Langerhans surround the hollow fiber. The hollow fiber and islets are surrounded by a housing comprising a semipermeable membrane having a pore size small enough to offer protection to the islets and host from immune reactive substances.

U.S. Pat. No. 5,702,444 to Struthers et al., which is incorporated herein by reference, describes an implantable artificial endocrine pancreas comprising a reactive body of soft, plastic, biocompatible, porous hydratable material supporting a multiplicity of endocrine pancreatic islets in isolated spaced relationship from each other, and a microporous barrier membrane enveloping and supporting the body, in spaced relationship from the pancreatic islets therein and through which molecules having a molecular weight greater than 60,000 Daltons cannot penetrate.

U.S. Pat. No. 6,630,154 to Fraker et al., which is incorporated herein by reference, describes a composition including at least one glycosaminoglycan, e.g., CIS, at least one perfluorinated substance and at least one alginate, e.g., sodium alginate.

US Patent Application Publication 2004/0109302 to Yoneda et al., which is incorporated herein by reference, describes a plant cultivation method, including cultivating plants with irradiating pulsed light with a period of 2 microseconds to 1 millisecond and a duty ratio of 20% to 70%, using a light emitting diode that emits white light or light of two colors.

U.S. Pat. No. 5,381,075 to Jordan, which is incorporated herein by reference, describes a method for driving an immersed flashing light system to enhance algae growth. The flashing light system includes a plurality of light source elements that are arranged to illuminate the algae. The light source elements are electrically connected to form banks of light source elements. Power is supplied to each bank of light sources in a predetermined sequence at regular intervals to substantially evenly supply each bank of light source elements with a series of power pulses, while maintaining a substantially continuous load on the power supply. The power pulses are substantially half cycles of a square wave.

PCT Publication WO 03/011445 to Monzyk et al., which is incorporated herein by reference, describes a photolytic cell and a photolytic artificial lung incorporated the photolytic cell.

PCT Publication WO 90/15526 to Kertz, which is incorporated herein by reference, describes an integument and related process for the culturing and growing of living organic material. The integument includes a cellule made of a gas-permeable, liquid- and contaminant-impermeable membrane for completely enclosing and sealing the culture from biological contaminants in the ambient environment. The membrane allows gas exchange between the living organic material and the ambient environment to provide enhanced growth and the prevention of contamination.

PCT Publication WO 01/50983 to Vardi et al., and U.S. patent application Ser. No. 10/466,069 in the national phase thereof, which are incorporated herein by reference, describe an implantable device comprising a chamber for holding functional cells and an oxygen generator for providing oxygen to the functional cells. In one embodiment, the oxygen generator comprises photosynthetic cells that convert carbon dioxide to oxygen when illuminated. In another embodiment, the oxygen generator comprises electrodes that produce oxygen by electrolysis. In another embodiment, an implantable chamber is used as part of a system for detecting or monitoring the level of a substance in body fluids. Such a system includes a detector adapted to monitor a property of the functional cells that is correlated with the level of the substance in the medium surrounding the functional cells.

Wu H et al., in "In situ electrochemical oxygen generation with an immunoisolation device," Ann N Y Acad Sci 875: 105-25 (1999), which is incorporated herein by reference, describe an in situ electrochemical oxygen generator which decomposes water electrolytically to provide oxygen to the adjacent planar immunobarrier diffusion chamber. In vitro culture experiments were carried out with beta TC3 cells encapsulated in titanium ring devices. The growth and viability of cells with or without in situ oxygen generation was studied.

Methods for immunoprotection of biological materials by encapsulation are described, for example, in U.S. Pat. Nos. 4,352,883, 5,427,935, 5,879,709, 5,902,745, and 5,912,005, all of which are incorporated herein by reference. The encapsulating material is typically selected so as to be biocompatible and to allow diffusion of small molecules between the cells of the environment while shielding the cells from immunoglobulins and cells of the immune system. Encapsulated beta cells, for example, can be injected into a vein (in which case they will eventually become lodged in the liver) or embedded under the skin, in the abdominal cavity, or in other locations. Fibrotic overgrowth around the implanted cells, however, gradually impairs substance exchange between the cells and their environment. Hypoxia of the cells typically leads to cell death.

PCT Patent Publication WO 01/50983 to Bloch et al., which is incorporated herein by reference, describes methods and apparatus for monitoring physiological variables in a living organism by implanting, inside a patient, functional tissue or cells, which are enclosed in a membrane permeable to glucose and other nutrients but impermeable to immune system cells. In order to maintain a sufficient oxygen supply for the functional cells an oxygen generator comprising photosynthetic cells and a light source is placed inside the membrane. In an application described in the '983 publication, an implantable chamber is used as part of a system for detecting or monitoring the level of a substance in body fluids. Such a system includes a detector adapted to monitor a property of the functional cells that is correlated with the level of the substance in the medium surrounding the functional cells.

PCT Publication WO 04/051774 to Minteer et al., which is incorporated herein by reference, describes bioanodes comprising a quaternary ammonium treated Nation(R) polymer membrane and a dehydrogenase incorporated within the treated Nation(R) polymer. The dehydrogenase catalyzes the oxidation of an organic fuel and reduces an adenine dinucleotide. The ion conducting polymer membrane lies juxtaposed to a polymethylene green redox polymer membrane, which serves to electro-oxidize the reduced adenine dinucleotide.

An article by Khamsi R, entitled, "Microbes Pass Valuable Gas," Wired News, May 20, 2003, describes the use of microorganisms to power fuel cells, such as by using baker's yeast (aerobic metabolism), algae (photosynthesis), and bacteria.

An article by Parikh et al., entitled, "Role of Spirulina in the control of glycemia and lipidemia in type 2 diabetes mellitus," J Med Food 2001, Winter 4(4): 193-199, which is incorporated herein by reference, describes a study aimed to evaluate the hypoglycemic and hypolipidemic role of Spirulina. Twenty-five subjects with type 2 diabetes mellitus were randomly assigned to receive Spirulina (study group) or to form the control group. The efficacy of Spirulina (supplementation (2 g/day for 2 months) was determined using the preintervention and postintervention blood glucose levels, glycosylated hemoglobin (HbA(1c)) levels, and lipid profiles of the diabetic subjects. Two-month supplementation with Spirulina resulted in an appreciable lowering of fasting blood glucose and postprandial blood glucose levels.

The following references, which are incorporated herein by reference, may be of interest:

Katz E et al., "Biochemical fuel cells," Chapter 21 of Handbook of Fuel Cells—Fundamentals, Technology and Applications, Vielstich W et al, eds., Volume 1: Fundamentals and Survey of Systems, John Wiley & Sons (2003)

Haselkorn A, "Microbial fuel cells to power future: new design promises medical breakthroughs," The Daily Californian Online, Aug. 28, 2002.

Fehr M et al., "In vivo imaging of the dynamics of glucose uptake in the cytosol of COS-7 cells by fluorescent nanosensors," J. Biol. Chem., 278(21):19127-19133 (2003)

Pescovitz D, "Body battery," Lab Notes—Research from the College of Engineering, University of California, Berkeley, Vol. 2, Issue 6 (August 2002)

Lam K B et al, "A micro photosynthetic electrochemical cell" Micro Electro Mechanical Systems, 2003. MEMS-03 Kyoto. IEEE The Sixteenth Annual International Conference on, pp. 391-394 (ISSN: 1084-6999) (Jan. 19-23, 2003)

T. Yagishita, T. Horigome, and K. Tanaka, "Effects of light, $CO_2$, and inhibitors on the current output of biofuel cells containing the photosynthetic organism Synechococcus sp.," J. Chem. Tech. Biotech, vol. 56, no. 4, pp. 393-399, 1993.

T. Yagishita, T. Horigome, K. Tanaka, "Biofuel-cells containing photosynthetic microorganisms," J. Electrochem. Soc. Japan, vol. 61, no. 6, pp. 687-688, 1993.

T. Yagishita, S. Sawayama, K.-I. Tsukahara, and T. Ogi, "Photosynthetic bio-fuel cell using cyanobacteria," Renewable Energy, vol. 9, no. 1-4, pp. 958-961, 1996.

T. Yagishita, S. Sawayama, K.-I. Tsukahara, and T. Ogi, "Effects of glucose addition and light on current outputs in photosynthetic electrochemical cells using Synechocystis sp. PCC6714," J. Biosci. Bioeng., vol. 99, no. 2, pp. 210-214, 1999.

R. M. Allen and H. P. Bennetto, "Microbial fuel cells: electricity production from carbohydrates," Appl. Biochem. Biotech., vol. 39/40, pp. 27-40, 1993.

X. Zhang and A. Halme, "Modelling of a microbial fuel cell process," Biotechnology Letters, vol. 17, no. 8, pp. 809-814, 1995.

A. Halme, X. Zhang and A. Ranta, "Study of biological fuel cells," in Proc. 2nd Annual Advances in R&D: The Commercialization of Small Fuel Cells and Battery Technologies for Use in Portable Applications, New Orleans, USA, Apr. 26-28, 2000, pp. 108-117.

K. B. Lam, E. Johnson, and L. Lin, "A Bio-Solar Cell Powered By Sub-Cellular Plant Photosystems," in Proc. IEEE Conf. on Micro Electro Mechanical Syst. (MEMS 2004), Maastricht, The Netherlands, Jan. 25-29, 2004, pp. 220-223.

A. Solovev, E. Katz, A. Shkuropatov, V. Shuvalov, and Y. Erokhin, "Conversion of light energy into electrical one using reaction centers from photosynthetic bacteria," Photosynth. Res., vol. 34, no. 1, pp. 126, 1992.

E. Y, Katz, A. Y. Shkuropatov, and V. A. Shuvalov, "Electrochemical approach to the development of a photoelectrode on the basis of photosynthetic reaction centers," Bioelectrochem. Bioenerg., vol. 23, pp. 239-247, 1990.

N. Mano, F. Mao, and A. Heller, "Characteristics of a miniature compartment-less glucose-O2 biofuel cell and its operation in a living plant," J. Am. Chem. Soc., vol. 125, no. 21, pp. 6588-6594, 2003.

M. Chiao, K. B. Lam, Y.-C. Su, and L. Lin, "A Miniaturized Microbial Fuel Cell," Technical Digest of Solid-State Sensors and Actuators Workshop, Hilton Head Island, June 2002, pp. 59-60.

M. Chiao, K. B. Lam, and L. Lin, "A microfabricated microbial fuel cell," in Proc. IEEE Conf. on Micro Electro Mechanical Syst. (MEMS 2003), Kyoto, Japan, Jan. 19-23, 2003, pp. 383-386.

E. Y. Katz, A. Y. Shkuropatov, O. I. Vagabova, and V. A. Shuvalov, "Coupling of photoinduced charge separation in reaction centers of photosynthetic bacteria with electron-transfer to a chemically modified electrode," Biochima et Biophysica Acta., vol. 976, pp. 121-128, 1989.

T. Yagishita, S. Sawayama, K.-I. Tsukahara, and T. Ogi, "Effects of intensity of incident light and concentrations of *Synechococcus* sp. and 2-hydroxy-1,4-naphthoquinone on the current output of photosynthetic electrochemical cell," Solar Energy, vol. 61, no. 5, pp. 347-353, 1997.

T. Yagishita, S. Sawayama, K.-I. Tsukahara, and T. Ogi, "Performance of photosynthetic electrochemical cells using immobilized *Anabaena variabilis* M-3 in discharge/culture cycles," J. Ferment. Bioeng., vol. 85, no. 5, pp. 546-549, 1998.

S. Tsujimura, A. Wadano, K. Kano, and T. Ikeda, "Photosynthetic bioelectrochemical cell utilizing cyanobacteria and water-generating oxidase," Enzyme and Microbial Technology, vol. 29, no. 5, pp. 225-231, 2001.

A. A. Solovev, E. Y. Katz, V. A. Shuvalov, and Y. E. Erokhin, "Photoelectrochemical effects for chemical modified platinum electrodes with immobilized reaction centers from *Rhodobacter sphaerides* R-26," Bioelectrochem. Bioenerg., vol. 26, pp. 29-41, 1991.

E. Y. Katz, and A. A. Solovev, "Photobioelectrodes on the basis of photosynthetic reaction centers. Study of exogenous quinines as possible electron transfer mediators," Anal. Chim. Acta., vol. 266, pp. 97-106, 1992.

T. Akiba, H. P. Bennetto, J. L. Stirling, and K. Tanaka, "Electricity production from alkalophilic organisms," Biotechnol. Letters, vol. 9, no. 9, pp. 611-616, 1987.

H. P. Bennetto, "Electricity generation by microorganisms," Biotech. Education, vol. 1, no. 4, pp. 163-169, 1990.

A. Halme, X. Zhang and N. Rintala, "Monitoring and control of a bacteria fuel cell process by colour analysis," in Proc. 7th Int. Conf. Computer Applications on Biotechnology, Osaka, Japan, May 31-Jun. 4, 1998, pp. 467-462.

Diabetes is a disorder that affects many people and results from the inability of the body to properly utilize and metabolize carbohydrates, particularly glucose. Normally the balance between glucose in the blood and glucose in body tissue cells is maintained by insulin, a hormone produced by the pancreas that controls the transfer of glucose from the blood into body tissue cells. Abnormal levels of glucose in the blood cause many complications and pathologies, leading to premature death in many cases.

Abnormally high levels of blood glucose can be controlled in many cases by the injection of insulin into the body. The amount of insulin to be injected depends upon the level of glucose in the blood, leading to a demand for accurate blood glucose sensors. Since regular monitoring of blood glucose levels allows for better regulation via insulin injections, it is desirable to have a simple and convenient means for monitoring blood glucose levels. Historically, the most common method to determine blood glucose levels was to obtain a small blood sample by piercing the finger and then placing the blood in an analyzer.

To avoid the regular piercing of a finger and to obtain more continuous monitoring of blood glucose levels, implantable glucose sensors have been described. In some cases, implantable sensors have been described that include cells such as transplanted pancreatic cells. These pancreatic cells are described as responding in a manner proportional to blood glucose levels, such that by monitoring the cellular response a blood glucose level can be determined. Several patents and applications using these techniques are discussed hereinbelow.

SUMMARY OF THE INVENTION

In some embodiments of the present invention, a device for determining the level of a substance in the blood or in another body fluid of a patient comprises a semi-permeable barrier such as a membrane, which is adapted to be implanted in the body of a patient and to enclose one or more types of microorganisms and a sensor. Examples of substances that are to be sensed include specific chemical compounds, blood glucose levels, lipids, electrolyte levels, and/or levels of various hormones. The microorganisms respond to the specific compound in the blood by generating a measurable response that can be detected by the sensor. By way of example, if algae are exposed to glucose, the algae will perform aerobic respiration, consuming oxygen while breaking down the glucose by glycolysis into carbon dioxide and water. This in turn leads to measurable changes in carbon dioxide and oxygen levels within the device, which can be detected by sensors. Thus, a difficult to measure substance (glucose) can be measured indirectly by measuring the level of an easy to measure substance (oxygen or carbon dioxide) that changes as the algae metabolize the glucose.

Typically, the membrane is adapted to allow the passage of nutrients, such as glucose, and other small molecules through the membrane, while inhibiting the passage of immune systems cells through the membrane. Examples of suitable membrane materials include polysulfone and polyurethane, among others. Isolation of the microorganisms from the immune system of the patient prevents the immune system from destroying the microorganisms and also reduces the tendency of the microorganisms to trigger an immune response.

Alternatively or additionally, the semi-permeable barrier comprises a matrix, which serves to contain the microorganisms and to isolate the microorganisms from the immune system. Typically, the matrix comprises a polymer and/or alginate, though other materials could be used.

The semi-permeable barrier also serves to contain the microorganisms, such that they cannot travel to other parts of the body. Additionally, the semi-permeable barrier provides a physical barrier limiting the number of microorganisms in the device due to the limited space inside the semi-permeable barrier. Further additionally, the semi-permeable barrier supports a gradient between the chemical concentrations inside the semi-permeable barrier and the body fluid outside the semi-permeable barrier.

Typically, the microorganisms comprise individuals from one or more of various species of algae. For example, spirulina and/or chlorella are species of algae that may be used in the device. Alternatively or additionally, various species of fungus, yeast, and bacteria, or some combination thereof are used as the microorganisms. In order to facilitate operation of the sensor, the microorganisms typically exhibit a response to the level of the specific compound in the blood or other body fluid that is measurable by the sensor.

Measurable responses typically comprise physiological responses of the microorganisms to levels of the specific compound. For example, increased glucose levels typically lead to increased glycolysis activity by the microorganisms, which results in increased energy release by the microorganisms and a temperature increase in the device. Thus, temperature within the device is used in some embodiments to indicate glucose levels. Additionally, optical changes induced by the response of the microorganisms to glucose levels facilitates the measurement of blood glucose levels, in some embodiments of the invention. For example, the scattering or absorption of light due to the microorganisms or the medium within which the cells reside typically changes in response to varying glucose levels. In addition, spectroscopy techniques provide quantification of glucose changes, as well as the quantification of other blood components such as hemoglobin or hematocrit, for the detection of patient anemia.

Alternatively or additionally, measurable responses comprise chemical responses of the microorganisms to levels of the specific compound. For example, as described hereinabove, increased glucose levels lead to increased microorganism respiratory metabolism, which results in a decrease in oxygen and an increase in carbon dioxide levels. Thus, by monitoring oxygen and/or carbon dioxide levels, a measure of the glucose level is attained. Other chemical species that can be monitored to deduce the level of the specific compound include electrolytes, enzymes, carbohydrates, lipids, and amino acids, along with other chemical species produced or consumed by cellular metabolism. Additionally, for some microorganisms, e.g., yeast, the level of glucose can be determined by monitoring the level of alcohol within the semi-permeable barrier, as yeast produces alcohol in the presence of glucose.

Further alternatively or additionally, measurable responses comprise electrical responses of the microorganisms to levels of the specific compound. Typically, the electrical conductivity across a portion of the device containing the microorganisms varies in response to the metabolic activity of the microorganisms, so by placing electrodes on opposing sides of the device the level of the specific compound can be inferred. Alternatively or additionally, physiological electrical activity of the microorganisms is measured, and a determination of blood glucose level is made responsive thereto.

For some embodiments of the current invention, the microorganisms comprise photosynthetic organisms. In a configuration, the device does not comprise a light source. Typically, however, the device comprises a light source, which is adapted to provide intermittent light to the photosynthetic organisms such that photosynthesis occurs. Typically, the device comprises a controller, which is coupled to the light source, such that the light source can be turned on and off. In a typical mode of operation, the controller pulses the light, such that when the light is on the photosynthetic organisms produce glucose and oxygen, while when the light is off photosynthesis ceases and the organisms consume the glucose that had crossed the membrane from the body as well as the glucose generated by photosynthesis. Measurements are typically taken while the light source is off and the organisms are consuming the glucose within the device. Typically, the measurements comprise measurements of oxygen levels and/or carbon dioxide levels, but other measurable quantities that characterize glucose metabolism may also be used, as discussed hereinabove. Once the measurements are complete, the light source is turned back on such that the photosynthetic organisms can replenish the oxygen level within the device, to maintain the health and proper function of the photosynthetic organisms. It is noted that for at least some of these embodiments, use of the light source is not integrally related to the sensing functionality of the device, but is instead related to maintaining the photosynthetic organisms in good health.

For some other embodiments of the present invention, the microorganisms comprise both photosynthetic organisms and non-photosynthetic organisms. The photosynthetic organisms provide oxygen to the device by means of photosynthesis, while the non-photosynthetic organisms consume the glucose within the device, and provide a measurable response to the glucose level.

For some embodiments of the present invention, the device is coupled to an insulin pump, which supplies insulin to the body in response to the glucose level determined by the device.

For some embodiments of the present invention, the device comprises a transmitter, which is adapted to transmit the measurements from the device to an external receiver.

For some embodiments of the present invention, the device comprises two sensors, one sensor inside the semi-permeable barrier and one sensor outside the semi-permeable barrier, so as to facilitate the measurement of blood glucose levels. The two sensors measure the same quantity for some applications, while they measure different quantities for other applications. For example, both sensors could measure oxygen levels, or one sensor could measure the oxygen level while the other sensor measures the temperature.

In another embodiment of the present invention, a device for controlling blood glucose levels comprises a large mass of algae or other photosynthesizing cells, a light source, and a blood glucose sensor as described hereinabove. When the glucose sensor detects high glucose levels the light source is turned off, such that the cells metabolize the blood glucose, resulting in decreasing blood glucose levels. When the blood glucose level is low, the light source is turned to a high level such that the cells produce glucose, which can permeate through the semi-permeable barrier into the blood, alleviating the hypoglycemia. During normoglycemia, the light is maintained at an intermediate level, so as not to affect the blood glucose level. Typically, a level of the light source is controlled to maintain glucose homeostasis. As appropriate, the level may be a duty cycle of the light and/or an amplitude of the light. For some applications, these techniques are applied to treat (a) only hypoglycemia, (b) only hyperglycemia, or (c) in the same patient, hypoglycemia and hyperglycemia.

For some embodiments of the current invention, the device is placed into a body space (e.g., the abdomen), whereby the surrounding body fluids provide the glucose, lipids, electrolytes, or various hormones and chemicals that the device is adapted to detect. For some other embodiments of the present invention, the device comprises optional graft tubes, which are adapted to be anastomosed to the vascular system such that blood flows through the device due to the natural pressure gradient in the vascular system. For some applications, the graft tubes are anastomosed in line with or in parallel with a single vein (e.g., the radial vein of the arm), resulting in a relatively small pressure gradient across the device. For some other applications, one of the graft tubes is anastomosed to a vein, while the other graft tube is anastomosed to an artery, resulting in a relatively large pressure gradient across the device.

There is therefore provided, in accordance with an embodiment of the present invention, substance monitoring apparatus, including:

a semi-permeable barrier, adapted to be implanted in a body of a subject and to allow passage therethrough of a substance, while inhibiting passage therethrough of immune cells;

microorganisms, disposed within the semi-permeable barrier so as to produce a measurable response to a level of the substance; and a sensor, adapted to measure the measurable response and not to measure a response of any mammalian cells that may be disposed within the semi-permeable barrier.

In an embodiment, the microorganisms include fungus, yeast, algae, and/or bacteria.

In an embodiment, the semi-permeable barrier is adapted to be implanted in fluid communication with blood.

In an embodiment, the semi-permeable barrier is adapted to be implanted in fluid communication with interstitial fluid.

In an embodiment, the semi-permeable barrier includes a membrane shaped to define an outer surface of a chamber, and wherein the microorganisms are disposed with the chamber.

In an embodiment, the semi-permeable barrier includes a matrix, and wherein the microorganisms are disposed within the matrix.

In an embodiment, the sensor is adapted to measure an oxygen level within the semi-permeable barrier associated with metabolism by the microorganisms.

In an embodiment, the sensor is adapted to measure a carbon dioxide level within the semi-permeable barrier associated with metabolism by the microorganisms.

In an embodiment, the sensor is adapted to measure a property of light within the semi-permeable barrier responsive to metabolism by the microorganisms.

In an embodiment, the semi-permeable barrier is adapted to allow passage therethrough of glucose, whereby the microorganisms produce the measurable response responsive to a level of the glucose.

In an embodiment, the semi-permeable barrier is adapted to allow passage therethrough of hemoglobin, whereby the microorganisms produce the measurable response responsive to a level of the hemoglobin.

In an embodiment, the microorganisms include two different types of microorganisms.

In an embodiment, the apparatus includes a transmitter, adapted to convey data responsive to the sensor measurement to a site external to the apparatus.

There is also provided, in accordance with an embodiment of the present invention, a protein including:
 a glucose binding site;
 cyan fluorescent protein (CFP); and
 yellow fluorescent protein (YFP),
wherein the protein is configured such that binding of glucose to the glucose binding site causes a reduction in a distance between the CFP and the YFP.

In an embodiment, the protein is encoded by an isolated nucleic acid fragment having a nucleotide sequence represented by Sequence No. 1 (SEQ ID NO: 1).

There is further provided, in accordance with an embodiment of the present invention, apparatus for detecting a concentration of a substance in a subject, the apparatus including a housing adapted to be implanted in the subject, the housing including:
 a fluorescence resonance energy transfer (FRET) measurement device; and
 cells genetically engineered to produce, in situ, a FRET protein having a FRET complex including a fluorescent protein donor, a fluorescent protein acceptor, and a binding site for the substance.

There is further provided, in accordance with an embodiment of the present invention, apparatus including a biofuel cell, adapted to be implanted in a body of a subject in fluid communication with blood of the subject, the biofuel cell including:
 an electrolyte membrane;
 an anode, coupled to the membrane;
 photosynthetic cells that photosynthetically generate oxygen using water present in the blood;
 a light source, adapted to illuminate the photosynthetic cells; and
 an oxygen cathode, coupled to the membrane, and adapted to use the oxygen as a reagent.

In an embodiment, the photosynthetic cells include algae. For some applications, the photosynthetic cells are loaded into the oxygen cathode.

In an embodiment, the apparatus is adapted to power the light source using a portion of energy generated by the biofuel cell.

In an embodiment, the anode is adapted to use a substance in the blood as a reagent, and the apparatus is adapted to determine a concentration of the substance in the blood responsively to a level of power output by the biofuel cell.

In an embodiment, the apparatus includes fuel-generating cells that biosynthetically generate a fuel, using a constituent of the blood as an input, and the anode is adapted to use the fuel as a reagent.

There is yet further provided, in accordance with an embodiment of the present invention, apparatus including a biofuel cell, adapted to be implanted in a body of a subject in fluid communication with blood of the subject, the biofuel cell including:
 an electrolyte membrane;
 a cathode, coupled to the membrane;
 cells that biosynthetically generate a fuel, using a constituent of the blood as an input; and
 an anode, coupled to the membrane, and adapted to use the fuel as a reagent.

In an embodiment, the cells include algae. For some applications, the cells are loaded into the anode.

For some applications, the fuel includes ethanol, and the cells generate the ethanol. For some applications, the constituent includes glucose, and the cells generate the fuel using the glucose as the input.

In an embodiment, the apparatus is adapted to determine a concentration of the constituent in the blood responsively to a level of power output by the biofuel cell.

There is still further provided, in accordance with an embodiment of the present invention, a cell genetically engineered to express glucose oxidase (GOx) in situ.

There is also provided, in accordance with an embodiment of the present invention, a method including:
 implanting cells in a subject; and
 subsequently administering, to the subject, a drug capable of killing the cells.

There is additionally provided, in accordance with an embodiment of the present invention, a method including:
 implanting cells in a subject;
 administering, to the subject, a promoter that regulates protein expression of the cells.

There is further provided, in accordance with an embodiment of the present invention, a method including implanting a glucose sensor in cerebral spinal fluid (CSF) of a spinal cord of a subject.

There is yet further provided, in accordance with an embodiment of the present invention, a method including:
 implanting an active medical device inside bone of a subject; and
 detecting or affecting a property of blood in fluid communication with the medical device.

There is still further provided, in accordance with an embodiment of the present invention, apparatus including a sensor, adapted to be implanted in a subject, the sensor including an electrical circuit that includes a material that has binding sites for a substance, such that binding of the substance to the material changes an electrical property of the material, the sensor adapted to determine a concentration of the substance responsively to the electrical property of the material.

In an embodiment, the material includes a polymer. For some applications, the substance includes blood glucose. For some applications, the electrical property includes electrical conductivity of the material.

There is also provided, in accordance with an embodiment of the present invention, a method including:
 implanting, in a subject, cells that are genetically engineered to express a promoter that is inducible by a substance; and
 administering the substance to the subject.

The present invention will be more fully understood from the following detailed description of embodiments thereof, taken together with the drawings, in which:

BRIEF DESCRIPTION OF THE DRAWINGS

FIG. 3 is a schematic illustration of apparatus for monitoring blood glucose levels, in accordance with an embodiment of the present invention.

DETAILED DESCRIPTION OF EMBODIMENTS

Figure 1:
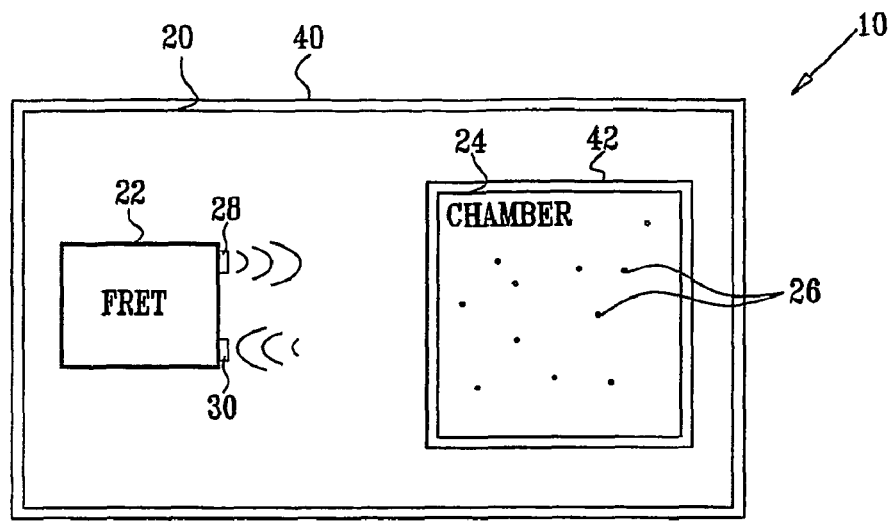
FIG. 1 is a schematic illustration of an implantable device for detecting a concentration of a substance in a subject, in accordance with an embodiment of the present invention.

FIG. 1 is a schematic illustration of an implantable device 10 for detecting a concentration of a substance in a subject, such as a blood constituent or other body fluid constituent of the subject, in accordance with an embodiment of the present invention. Device 10 comprises an implantable housing 20 that holds a fluorescence resonance energy transfer (FRET) measurement device 22 and cells 26. FRET measurement device 22 comprises a light source 28, such as a laser, and a FRET detector 30. Cells 26 are genetically engineered to produce, in situ, a FRET protein having a FRET complex comprising a fluorescent protein donor, a fluorescent protein acceptor, and a binding site for the substance. The FRET complex is configured such that binding of the substance to the binding site changes the configuration of the complex, and thus the distance between the donor and the acceptor. FRET detector 30 detects this change in distance to determine the quantity of the FRET complex in each of the two configurations, thereby enabling a calculation of the concentration of the substance. Typically, cells 26 comprise slowly-dividing cells, such as, for example, beta cells, neuronal cells, or liver cells.

For some applications, the substance includes glucose, and the binding site is a glucose binding site. For some applications, the concentration of the substance is calculated by calculating a ratio of an emission level of the donor at a first wavelength to an emission level of the acceptor at a second wavelength.

For some applications, the fluorescent protein donor includes cyan fluorescent protein (CFP), and the fluorescent protein acceptor includes yellow fluorescent protein (YFP). Alternatively or additionally, the protein comprises another donor/acceptor pair, such as blue fluorescent protein (BFP)/green fluorescent protein (GFP), GFP/Rhodamine, FITC/Cy3, FITC/Rhodamine, or another pair in which the donor emission spectrum overlaps the excitation spectrum of the acceptor. For some applications, the FRET complex includes one or more flexible hinge regions that enable the winding of large molecules, so as to enable energy transfer between the donor and the acceptor.

In an embodiment of the present invention, the FRET protein is encoded by an isolated nucleic acid fragment having a nucleotide sequence represented by Sequence No. 1 (SEQ ID NO: 1). For some applications, the FRET protein further comprises a leading peptide that directs the protein to the cell membrane, such as represented by Sequence No. 2 (SEQ ID NO: 2).

For some applications, implantable device 10 comprises a chamber 24, which holds cells 26. Alternatively, the cells are held directly in housing 20. For some applications, the cells are placed in a matrix, while for other applications, the cells are placed in suspension.

In an embodiment of the present invention, implantable device 10 comprises a first membrane 40, placed around housing 20, such that the membrane separates the housing from the body of the subject. For some applications, first membrane 40 is configured to prevent passage therethrough of cells, such as white blood cells, while allowing passage of the FRET protein out of housing 20, typically into blood surrounding the housing, where the protein breaks down. For example, the first membrane may be configured to allow passage only of molecules smaller than about 50 kilodalton. Such a membrane is typically used for applications in which the FRET protein is engineered to have a high affinity for the substance, such that the substance generally remains irreversibly bound to the protein. In order to maintain the accuracy of the concentration determination even as the concentration of the substance in the body drops, the FRET protein is allowed to exit housing 20. In these applications, cells 26 are typically configured to continuously generate quantities of the FRET protein sufficient to replace the protein that escapes.

In an embodiment of the present invention, first membrane 40 is configured to additionally prevent passage therethrough of the FRET protein, while allowing fragments of the protein to exit housing 20 as the protein is naturally broken down. Such a membrane is typically used for applications in which the FRET protein is engineered to have a medium affinity for the substance, such that the substance reversibly binds to the protein at high concentrations of the substance, and detaches from the protein at lower concentrations of the substance (similar to the reversible concentration-dependent binding of oxygen to hemoglobin). In this embodiment, cells 26 are typically configured to produce lower quantities of the FRET protein than in embodiments in which first membrane 40 is configured to allow passage of FRET protein therethrough For some applications in which implantable device 10 comprises chamber 24, chamber 24 is surrounded by a second membrane 42, which is typically configured to prevent passage of cells 26 therethrough, but allow passage of FRET protein and/or fragments thereof, as appropriate for the application. For some applications, FRET measurements are made when the protein is outside of chamber 24 in housing 20. For other applications, the FRET protein remains within chamber 24 while FRET measurements are made thereof. For example, cells 26 and the FRET protein may be configured such that the FRET protein remains contained within cells 26 in chamber 24. Alternatively or additionally, cells 26 and the FRET protein may be configured such that the FRET protein becomes positioned on the cell membrane of the cells.

Figure 2:
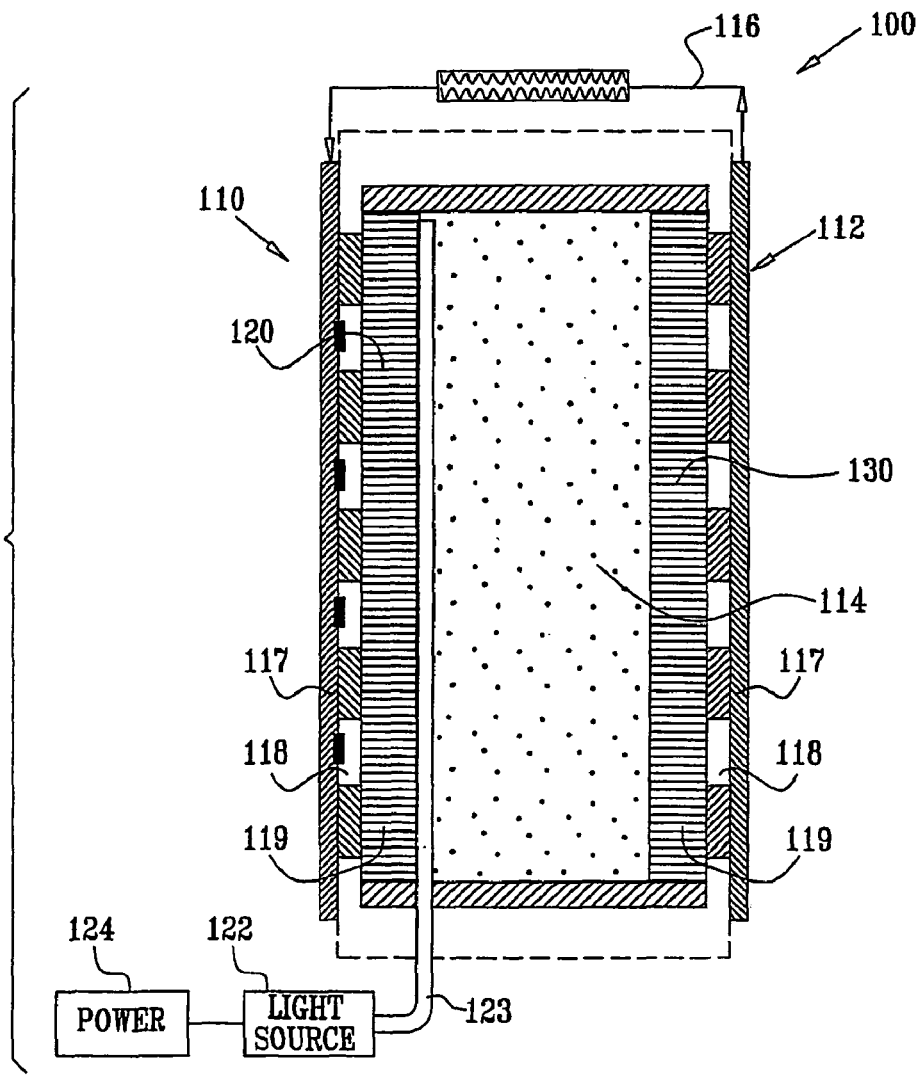
FIG. 2 is a schematic illustration of an implantable biofuel cell in accordance with an embodiment of the present invention.

Reference is now made to FIG. 2, which is a schematic illustration of an implantable biofuel cell 100, in accordance with an embodiment of the present invention. Biofuel cell 100 is adapted to be implanted in a body of a subject, such as in, or in fluid communication with, a blood vessel, peritoneum, or other body chamber. Biofuel cell 100 is similar in some respects to a conventional fuel cell, such as a conventional direct ethanol fuel cell. However, unlike a conventional fuel cell, biofuel cell 100 generates one or both of the reactants (oxygen and the fuel) using at least one biological process that has as a reagent a substance available in blood serum or in another body fluid. Biofuel cell 100 typically comprises an oxygen cathode 110, an ethanol anode 112, and an electrolyte membrane 114. Alternatively, for some applications, anode 112 uses another fuel, such as glucose, or an alcohol other than ethanol, e.g., methanol.

In embodiments in which anode 112 uses ethanol as its fuel, the following reaction occurs at the anode:

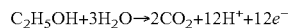

The electrons are conducted through a circuit 116 to cathode 110, while the hydrogen ions are transported across membrane 114 to cathode 110. At cathode 110, the follow reaction occurs:

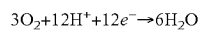

Each of the electrodes typically comprises three layers: a current collector plate 117, an intermediary layer 118, and a porous active layer 119.

In an embodiment of the present invention, biofuel cell 100 comprises photosynthetic cells 120 that photosynthetically generate the oxygen used by cathode 110. Photosynthetic cells 120 typically comprise algae. Typically, photosynthetic cells 120 are loaded into cathode 110 (either in active layer 119 and/or in collector plate 117). Alternatively, the photosynthetic cells are held in a separate chamber in a vicinity of the cathode (configuration not shown). Biofuel cell 100 comprises a light source 122 that is adapted to provide light for the photosynthetic cells, such as via at least one optical fiber 123. The photosynthetic cells typically use water present in blood serum for photosynthesis. Alternatively, for some applications, biofuel cell 100 uses electrolysis for generating oxygen (for example, using techniques described in the above-mentioned '592 patent and/or '427 patent application publication to Colton et al.). Optionally, the electrolysis is powered by a portion of the energy generated by the biofuel cell.

For some applications, light source 122 is powered by a portion of the energy generated by biofuel cell 100. Alternatively, the biofuel cell comprises a power source 124, such as a battery, a rechargeable battery, a capacitor, or a coil adapted to be inductively coupled to an external coil. For some applications, power source 124 provides power to the light source during the entire time the light source operates. For other applications, power source 124 provides power to the light source only during an initial activation period of the fuel cell, and thereafter, once the fuel cell generates sufficient power, the fuel cell powers the light source. For these applications, the fuel cell optionally recharges the power source.

In an embodiment of the present invention, biofuel cell 100 comprises cells 130 that biosynthetically generate the ethanol used by anode 112. Cells 130 typically comprise algae or yeast. For some applications, cells 130 comprises the same type of algae as photosynthetic cells 120. Typically, cells 130 are loaded into anode 112 (either in active layer 119 and/or in collector plate 117). Alternatively, the cells are held in a separate chamber in a vicinity of the anode (configuration not shown). Cells 130 typically use glucose present in blood serum as an input for their biosynthesis of ethanol. For some applications, anode 112 comprises one or more elements selected from the list consisting of: platinum, ruthenium, and carbon. For some applications, cells 130 are separated from blood serum by a membrane that limits the rate of passage of glucose from the serum to the cells. For example, the membrane may surround anode 112. For some applications, anode 112 or the chamber holding the cells, as appropriate, additionally comprise one or more enzymes to catalyze the reactions.

In an embodiment of the present invention, to remove $CO_2$ that may coat the electrodes of biofuel cell 100 over time, the biofuel cell intermittently illuminates cells 130, e.g., once per second, per hour, or per day. The cells generate $O_2$, which cleans the $CO_2$ from the electrodes.

For some applications, blood serum that enters the electrode compartments of cathode 110 and anode 112 by diffusion, natural flow, and/or convection is sufficient to maintain reagent concentrations necessary for operating the fuel cell at the desired power output level. For some applications in which greater reagent concentrations are desired, the fuel cell is configured to actively drive blood serum into the electrode compartments, such as with a pump.

For some applications, biofuel cell 100 achieves a greater than 5:1 ratio (e.g., an approximately 10:1 ratio) of power generated to power consumed by light source 112. For some applications, biofuel cell 100 produces between about 10 and about 20 mA per $cm^2$ of electrode surface area, while light source 122 consumes only about 1 mA per $cm^2$. It is estimated that to produce 1 mA (excluding the power consumption of the light source), cathode 110 consumes 5 micrograms of oxygen per minute, and anode 112 consumes 2.4 micrograms of ethanol per minute.

In an embodiment of the present invention, biofuel cell 100 is configured to function as a glucose sensor. The electrical current generated by the cell is related, e.g., linearly related within a range, to the glucose concentration in the blood serum. The cell comprises an analog or digital processor that measures the current, and, for some applications, calculates the glucose concentration responsively thereto. For some applications, the cell measures concentrations of blood components other than glucose.

For some applications, the biofuel cell transmits (typically wirelessly) the collected data to a portable electronic device, such as a cell phone or PDA, which is configured to present the data on a screen of the device. For some applications, the biofuel cell transmits raw data to the device, and the device is programmed (in hardware or software) to perform all or a portion of the processing necessary to translate the raw data into concentration data. For some applications, the device is configured to transmit the raw data or concentration data over a public wireless or wired communication network.

In an embodiment of the present invention, biofuel cell 100 is implanted in order to consume blood glucose of a subject, thereby reducing the blood glucose level. This technique may be used, for example, to treat subjects suffering from diabetes or hyperglycemia.

In an embodiment of the present invention, cells are genetically engineered to express glucose oxidase (GOx) in situ. Some implantable glucose sensors use GOx to convert blood glucose into gluconic acid. The gluconic acid is converted into oxygen, and the oxygen concentration is measured to determine the glucose concentration. The genetically engineered cells of this embodiment typically generate sufficient GOx to maintain an implantable blood glucose sensor for weeks or months. Alternatively, the cells are engineered to express another enzyme used to convert glucose into gluconic acid.

In an embodiment of the present invention, a method comprises administering to a patient a drug to kill cells implanted in the patient. For example, the implanted cells may eventually cease to function for their intended purpose, and so may need to be replaced. (In addition, some implanted cells may, under certain circumstances, escape from a chamber containing them, and therefore need to be eliminated.) For some applications, the drug is administered to the patient when the patient is asymptomatic with respect to the implanted cells. For some applications, the drug is administered to kill the cells while they are in an implanted chamber. For some applications, the method further comprises implanting the cells in the patient prior to administering the drug. For some applications, the drug is administered in conjunction with removing an implanted chamber from the patient's body (for example, to kill any cells that may escape during or prior to the removal procedure). Optionally, a new chamber is subsequently implanted. Alternatively, the implanted chamber is not removed from the patient's body, and the method comprises administering the drug to kill the cells in the chamber while it remains in the patient's body. For some applications, the drug includes a promoter, e.g., to control the expression of a gene. For some applications, the drug includes tetracycline. In an embodiment, the drug is administered systemically (e.g., intramuscularly, or intravenously), and travels to a site where the cells are located. Alternatively, the drug is administered directly to a site where the cells are located.

In an embodiment of the present invention, a method comprises administering, to a subject, a promoter that regulates protein expression of cells implanted in the subject. For some applications, the cells are implanted for sensing a concentration of a blood constituent. For some applications, a level of expression of the FRET protein described hereinabove is regulated, such as to optimize the FRET measurement. For some applications, the promoter is selected to reduce protein expression, for example, if the subject has a reaction to the protein.

In an embodiment of the present invention, a glucose sensor is adapted to be implanted in cerebral spinal fluid (CSF) of the spinal cord. Because the constituents of CSF are more tightly controlled than those of blood, there is generally less background noise in CSF that might reduce the accuracy of the sensor. For some applications, the techniques of this embodiment are practiced in conjunction with the glucose sensing techniques described herein, mutatis mutandis. Alternatively, these techniques are practiced in conjunction with implantable glucose sensors known in the art, mutatis mutandis.

In an embodiment of the present invention, a method comprises implanting an active medical device inside bone, and detecting or affecting a property of blood or another body fluid in fluid communication with the medical device. The lack of fibrosis inside bone generally results in good fluid communication between the medical device and the blood. For some applications, the medical device comprises a glucose sensor. For some applications, the bone includes bone of a tooth or bone of a long bone.

In an embodiment of the present invention, an implantable sensor is provided for sensing a concentration of a substance, the sensor comprising an electrical circuit that comprises a material that has binding sites for the substance, such that binding of the substance to the material changes an electrical conductivity or other electrical property of the material. The sensor measures the concentration of the substance by detecting the conductivity of the material in the circuit. For some applications, the material comprises a polymer. For some applications, the substance includes blood glucose. Typically, the modification of the material is reversible, such that the binding sites bind and unbind the substance depending on the level of the substance in contact with the material, e.g., in blood in contact with the material.

In an embodiment of the present invention, one or both opposing plates of a capacitor are coated with the material, such that the binding of the substance to the material changes the capacitance of the capacitor. This change is detectable, for example, by assessing changes in a discharge time of the capacitor, or by applying the equation $Q=CV$. Alternatively, the material is integrated into a resistor, such that the binding of the substance to the material changes a resistance of the resistor.

In an embodiment of the present invention, the material comprises a polymer produced by preparing a polymer mixture including the substance (e.g., glucose), and subsequently allowing the substance to dissolve out of the mixture. The sites of the polymer from which the substance dissolved preferentially bind the substance.

In an embodiment of the present invention, an internal surface of an implantable chamber comprises a material that has binding sites for a substance, such as glucose. The chamber is adapted to open, so as to allow blood to enter the chamber, thereby allowing the substance in the blood to bind to the material. The chamber is then closed, and cleansed of constituents other than the substance, which constituents do not bind to the material. This cleansing serves to reduce noise. For some applications, the material is integrated into an electrical circuit, as described hereinabove, and the concentration of the substance is measured by the circuit. Alternatively, this technique is used to generate the substance, e.g., glucose, for example, as fuel for a fuel cell, which is adapted to either measure the concentration of the substance, or to generate energy using the substance as fuel.

In an embodiment of the present invention, implantable cells are genetically engineered to express a promoter that is inducible by a substance administered to a body of a subject in which the cells are implanted. For some applications, the inducing substance includes an antibiotic. Typically, the promoter is capable of activating and/or deactivating one or more genes of interest.

FIG. 3 is a schematic illustration of a glucose sensing device 210, which is adapted to be implanted in the body of a patient, in accordance with an embodiment of the present invention. Device 210 comprises a semi-permeable barrier 212, such as a membrane, which is adapted to be implanted in the body of the patient and to contain one or more types of microorganisms 214 and a sensor 220. For example, when semi-permeable barrier 212 comprises a membrane, the membrane typically defines an outer surface of device 210, and microorganisms 214 are disposed within a space defined by the membrane. Typically, semi-permeable barrier 212 is adapted to allow the passage therethrough of nutrients, such as glucose, while inhibiting the passage therethrough of immune systems cells. Examples of suitable membrane materials include polysulfone and polyurethane, among others. Isolation of the microorganisms from the immune system of the patient prevents the immune system from destroying the microorganisms and also reduces the tendency of the microorganisms to trigger an immune system response.

Alternatively or additionally, semi-permeable barrier 212 comprises a matrix, in which the microorganisms are disposed, and which isolates the microorganisms from the immune system. Typically, the matrix comprises a polymer and/or alginate, though other materials could be used.

In an embodiment, microorganisms 214 comprise individuals from one or more of various species of algae. For example, spirulina and chlorella are species of algae that may be used in device 210. Alternatively or additionally, various species of fungus, yeast, and bacteria, or some combination thereof are used as the microorganisms. Microorganisms 214 typically exhibit a measurable response to blood glucose level, as discussed hereinabove.

In an embodiment, sensor 220 is adapted to determine the oxygen level within the device, since the oxygen level varies with glucose metabolism by microorganisms 214. Thus, as the blood glucose diffuses across semi-permeable barrier 212, the microorganisms metabolize the glucose, resulting in a decrease in the oxygen level in the device. The greater the level of glucose within the device, the more the oxygen level will decrease. Similarly, when blood glucose levels are lower, glucose levels within device 210 are also lower, and oxygen levels within device 210 are detected by sensor 220 to be higher. Alternatively or additionally, other parameters are measured by sensor 220, as described hereinabove.

For some applications, device 210 additionally comprises a light source 216, which is coupled to a controller 218. The sensor is also coupled to controller 218, and controller 218 is programmed such that if the oxygen level in the device becomes low enough to threaten the health of the microorganisms, the controller turns on the light source, initiating photosynthesis which results in the production of oxygen and rising oxygen levels in the device. Once the oxygen level is sufficiently high, the light source is turned off. Alternatively or additionally, the controller regulates the light source as described hereinabove.

For some embodiments of the current invention, device 210 is placed into a body space (e.g., the abdomen), whereby the surrounding body fluids provide the glucose that the device is adapted to detect. For some other embodiments of the present invention, device 210 comprises optional graft tubes 222, which are adapted to be anastomosed to the vascular system such that blood flows through the device due to the natural pressure gradient in the vascular system. For some applications, graft tubes 222 are anastomosed in line with or in parallel with a single vein (e.g., the radial vein of the arm), resulting in a relatively small pressure gradient across the device. For some other applications, one of graft tubes 222 is anastomosed to a vein, while the other one of graft tubes 222 is anastomosed to an artery, resulting in a relatively large pressure gradient across the device.

It will be appreciated by persons skilled in the art that the present invention is not limited to detecting blood glucose, but that blood glucose is used by way of example. The scope of the present invention includes determining and/or monitoring levels of other substances in the body.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for detecting a concentration of a substance in a subject, the apparatus comprising:
   a fluorescence resonance energy transfer (FRET) measurement device; and
   a housing adapted to be implanted in the subject, the housing comprising
   cells genetically engineered to produce, in situ, a FRET protein having a FRET complex comprising a fluorescent protein donor, a fluorescent protein acceptor, and a binding site for the substance.

2. The apparatus according to claim 1, wherein the protein that the cells are genetically engineered to produce comprises:
   a glucose binding site;
   cyan fluorescent protein (CFP); and
   yellow fluorescent protein (YFP),
   wherein the protein is configured such that binding of glucose to the glucose binding site changes a distance between the CFP and the YFP.

3. The apparatus of claim 2, wherein the protein is encoded by an isolated nucleic acid fragment having the nucleotide sequence in SEQ ID NO: 1.

4. The apparatus according to claim 1, comprising an inducer that is adminsterable to the subject and that regulates protein expression of the cells.

5. The apparatus according to claim 1, wherein the cells comprise beta or liver cells.

6. The apparatus according to claim 1, wherein the substance includes glucose, and wherein the binding site comprises a binding site for glucose.

7. The apparatus according to claim 1, wherein the protein comprises a protein selected from the group consisting of blue fluorescent protein (BFP), green fluorescent protein (GFP), and GFP/Rhodamine.

8. The apparatus according to claim 1, wherein the housing comprises a chamber which holds the cells.

9. The apparatus according to claim 1, wherein the cells are held directly within the housing, with no intervening chamber to hold the cells.

10. The apparatus according to claim 1, wherein the cells are disposed within a matrix.

11. The apparatus according to claim 1, wherein the cells are disposed in a suspension.

12. The apparatus according to claim 1, wherein the housing comprises a membrane that prevents passage therethrough of cells of the subject's body.

13. The apparatus according to claim 12, wherein the membrane is configured to prevent passage therethrough of the FRET protein.

14. The apparatus according to claim 1, wherein the cells are configured such that the protein produced by the genetically-engineered cells becomes positioned on the membranes of the cells.

15. The apparatus according to claim 14, wherein the protein comprises a targeting peptide that is configured to direct the protein to the membranes of the cells.

16. The apparatus according to claim 15, wherein the sequence of the targeting peptide is SEQ ID NO: 2.

17. The apparatus according to claim 1, comprising a drug capable of killing the cells, the drug being configured to be administered to the subject subsequently to the implantation of the housing in the subject.

18. The apparatus according to claim 1, wherein the fluorescence resonance energy transfer (FRET) measurement device is implantable in the subject.

19. The apparatus according to claim 18, wherein the housing comprises the fluorescence resonance energy transfer (FRET) measurement device.

* * * * *

SEQUENCE LISTING

```
<160> NUMBER OF SEQ ID NOS: 2

<210> SEQ ID NO 1
<211> LENGTH: 2349
<212> TYPE: DNA
<213> ORGANISM: Artificial Sequence
<220> FEATURE:
<223> OTHER INFORMATION: Artificial sequence comprising coding sequences
      from the following organisms: Aequorea victoria, and Escherichia
      coli K12, and linker sequences comprising: poly-Gly and
      restriction sites
<220> FEATURE:
<221> NAME/KEY: misc_feature
<222> LOCATION: (1)..(9)
<223> OTHER INFORMATION: Linker sequence containing a restriction site
      AAGCTT
<220> FEATURE:
<221> NAME/KEY: exon
<222> LOCATION: (10)..(726)
<223> OTHER INFORMATION: Cyan Fluorescent Protein, organism: Aequorea
      victoria
<220> FEATURE:
<221> NAME/KEY: misc_feature
<222> LOCATION: (727)..(744)
<223> OTHER INFORMATION: Linker sequence compising poly-Gly and a
      restriction site
<220> FEATURE:
<221> NAME/KEY: exon
<222> LOCATION: (745)..(1602)
<223> OTHER INFORMATION: Glucose-galactose binding protein, organism:
      Escherichia coli K12
<220> FEATURE:
<221> NAME/KEY: misc_feature
<222> LOCATION: (1603)..(1629)
<223> OTHER INFORMATION: Linker sequence comprising poly-Gly and
      restriction site GGATCC
<220> FEATURE:
<221> NAME/KEY: exon
<222> LOCATION: (1603)..(2349)
<223> OTHER INFORMATION: Yellow Fluorescent Protein, organism: Aequorea
      victoria, comprising stop codon "taa"

<400> SEQUENCE: 1 aagcttacc atg gtg agc aag ggc gag gag ctg ttc acc ggg gtg gtg ccc        51
          Met Val Ser Lys Gly Glu Glu Leu Phe Thr Gly Val Val Pro
          1               5                   10 atc ctg gtc gag ctg gac ggc gac gta aac ggc cac aag ttc agc gtg          99
Ile Leu Val Glu Leu Asp Gly Asp Val Asn Gly His Lys Phe Ser Val
15                  20                  25                  30 tcc ggc gag ggc gag ggc gat gcc acc tac ggc aag ctg acc ctg aag         147
Ser Gly Glu Gly Glu Gly Asp Ala Thr Tyr Gly Lys Leu Thr Leu Lys
                35                  40                  45
```

-continued

| | |
|---|---|
| ttc atc tgc acc acc ggc aag ctg ccc gtg ccc tgg ccc acc ctc gtg<br>Phe Ile Cys Thr Thr Gly Lys Leu Pro Val Pro Trp Pro Thr Leu Val<br>              50                      55                    60 | 195 |
| acc acc ctg acc tgg ggc gtg cag tgc ttc agc cgc tac ccc gac cac<br>Thr Thr Leu Thr Trp Gly Val Gln Cys Phe Ser Arg Tyr Pro Asp His<br>        65                      70                      75 | 243 |
| atg aag cag cac gac ttc ttc aag tcc gcc atg ccc gaa ggc tac gtc<br>Met Lys Gln His Asp Phe Phe Lys Ser Ala Met Pro Glu Gly Tyr Val<br>80                      85                      90 | 291 |
| cag gag cgc acc atc ttc ttc aag gac gac ggc aac tac aag acc cgc<br>Gln Glu Arg Thr Ile Phe Phe Lys Asp Asp Gly Asn Tyr Lys Thr Arg<br>95                   100                105              110 | 339 |
| gcc gag gtg aag ttc gag ggc gac acc ctg gtg aac cgc atc gag ctg<br>Ala Glu Val Lys Phe Glu Gly Asp Thr Leu Val Asn Arg Ile Glu Leu<br>             115                    120              125 | 387 |
| aag ggc atc gac ttc aag gag gac ggc aac atc ctg ggg cac aag ctg<br>Lys Gly Ile Asp Phe Lys Glu Asp Gly Asn Ile Leu Gly His Lys Leu<br>              130                  135              140 | 435 |
| gag tac aac tac atc agc cac aac gtc tat atc acc gcc gac aag cag<br>Glu Tyr Asn Tyr Ile Ser His Asn Val Tyr Ile Thr Ala Asp Lys Gln<br>             145                    150              155 | 483 |
| aag aac ggc atc aag gcc aac ttc aag atc cgc cac aac atc gag gac<br>Lys Asn Gly Ile Lys Ala Asn Phe Lys Ile Arg His Asn Ile Glu Asp<br>160                   165                170 | 531 |
| ggc agc gtg cag ctc gcc gac cac tac cag cag aac acc ccc atc ggc<br>Gly Ser Val Gln Leu Ala Asp His Tyr Gln Gln Asn Thr Pro Ile Gly<br>175                   180                185              190 | 579 |
| gac ggc ccc gtg ctg ctg ccc gac aac cac tac ctg agc acc cag tcc<br>Asp Gly Pro Val Leu Leu Pro Asp Asn His Tyr Leu Ser Thr Gln Ser<br>                 195                200              205 | 627 |
| gcc ctg agc aaa gac ccc aac gag aag cgc gat cac atg gtc ctg ctg<br>Ala Leu Ser Lys Asp Pro Asn Glu Lys Arg Asp His Met Val Leu Leu<br>             210                    215              220 | 675 |
| gag ttc gtg acc gcc gcc ggg atc act ctc ggc atg gac gag ctg tac<br>Glu Phe Val Thr Ala Ala Gly Ile Thr Leu Gly Met Asp Glu Leu Tyr<br>             225                    230              235 | 723 |
| aag ggaatccgcg gtggtggt gct gat act cgc att ggt gta aca atc tat<br>Lys                             Ala Asp Thr Arg Ile Gly Val Thr Ile Tyr<br>                                    240                    245 | 774 |
| aag tac gac gat aac ttt atg tct gta gtg cgc aag gct att gag caa<br>Lys Tyr Asp Asp Asn Phe Met Ser Val Val Arg Lys Ala Ile Glu Gln<br>250                   255                260              265 | 822 |
| gat gcg aaa gcc gcg cca gat gtt cag ctg ctg atg aat gat tct cag<br>Asp Ala Lys Ala Ala Pro Asp Val Gln Leu Leu Met Asn Asp Ser Gln<br>                 270                275              280 | 870 |
| aat gac cag tcc aag cag aac gat cag atc gac gta ttg ctg gcg aaa<br>Asn Asp Gln Ser Lys Gln Asn Asp Gln Ile Asp Val Leu Leu Ala Lys<br>             285                    290              295 | 918 |
| ggg gtg aag gca ctg gca atc aac ctg gtt gac ccg gca gct gcg ggt<br>Gly Val Lys Ala Leu Ala Ile Asn Leu Val Asp Pro Ala Ala Ala Gly<br>             300                  305              310 | 966 |
| acg gtg att gag aaa gcg cgt ggg caa aac gtg ccg gtg gtt ttc ttc<br>Thr Val Ile Glu Lys Ala Arg Gly Gln Asn Val Pro Val Val Phe Phe<br>             315                    320              325 | 1014 |
| aac aaa gaa ccg tct cgt aag gcg ctg gat agc tac gac aaa gcc tac<br>Asn Lys Glu Pro Ser Arg Lys Ala Leu Asp Ser Tyr Asp Lys Ala Tyr<br>330                    335                340              345 | 1062 |
| tac gtt ggc act gac tcc aaa gag tcc ggc att att caa ggc gat ttg<br>Tyr Val Gly Thr Asp Ser Lys Glu Ser Gly Ile Ile Gln Gly Asp Leu<br>             350                  355              360 | 1110 |

```
att gct aaa cac tgg gcg gcg aat cag ggt tgg gat ctg aac aaa gac     1158
Ile Ala Lys His Trp Ala Ala Asn Gln Gly Trp Asp Leu Asn Lys Asp
        365                 370                 375 ggt cag att cag ttc gta ctg ctg aaa ggt gaa ccg ggc cat ccg gat     1206
Gly Gln Ile Gln Phe Val Leu Leu Lys Gly Glu Pro Gly His Pro Asp
    380                 385                 390 gca gaa gca cgt acc act tac gtg att aaa gaa ttg aac gat aaa ggc     1254
Ala Glu Ala Arg Thr Thr Tyr Val Ile Lys Glu Leu Asn Asp Lys Gly
395                 400                 405 atc aaa act gaa cag tta cag tta gat acc gca atg tgg gac acc gct     1302
Ile Lys Thr Glu Gln Leu Gln Leu Asp Thr Ala Met Trp Asp Thr Ala
410                 415                 420                 425 cag gcg aaa gat aag atg gac gcc tgg ctg tct ggc ccg aac gcc aac     1350
Gln Ala Lys Asp Lys Met Asp Ala Trp Leu Ser Gly Pro Asn Ala Asn
        430                 435                 440 aaa atc gaa gtg gtt atc gcc aac aac gat gcg atg gca atg ggc gcg     1398
Lys Ile Glu Val Val Ile Ala Asn Asn Asp Ala Met Ala Met Gly Ala
    445                 450                 455 gtt gaa gcg ctg aaa gca cac aac aag tcc agc att ccg gtg ttt ggc     1446
Val Glu Ala Leu Lys Ala His Asn Lys Ser Ser Ile Pro Val Phe Gly
460                 465                 470 gtc gat gcg ctg cca gaa gcg ctg gcg ctg gtg aaa tcc ggt gca ctg     1494
Val Asp Ala Leu Pro Glu Ala Leu Ala Leu Val Lys Ser Gly Ala Leu
475                 480                 485 gcg ggc acc gta ctg aac gat gct aac aac cag gcg aaa gcg acc ttt     1542
Ala Gly Thr Val Leu Asn Asp Ala Asn Asn Gln Ala Lys Ala Thr Phe
490                 495                 500                 505 gat ctg gcg aaa aac ctg gcc gat ggt aaa ggt gcg gct gat ggc acc     1590
Asp Leu Ala Lys Asn Leu Ala Asp Gly Lys Gly Ala Ala Asp Gly Thr
        510                 515                 520 aac tgg aaa atc ggt ggt ggt gcg gat cca ccg gtc gcc atg gtg agc     1638
Asn Trp Lys Ile Gly Gly Gly Ala Asp Pro Pro Val Ala Met Val Ser
    525                 530                 535 aag ggc gag gag ctg ttc acc ggg gtg gtg ccc atc ctg gtc gag ctg     1686
Lys Gly Glu Glu Leu Phe Thr Gly Val Val Pro Ile Leu Val Glu Leu
540                 545                 550 gac ggc gac gta aac ggc cac aag ttc agc gtg tcc ggc gag ggc gag     1734
Asp Gly Asp Val Asn Gly His Lys Phe Ser Val Ser Gly Glu Gly Glu
555                 560                 565 ggc gat gcc acc tac ggc aag ctg acc ctg aag ttc atc tgc acc acc     1782
Gly Asp Ala Thr Tyr Gly Lys Leu Thr Leu Lys Phe Ile Cys Thr Thr
570                 575                 580                 585 ggc aag ctg ccc gtg ccc tgg ccc acc ctc gtg acc acc ttc ggc tac     1830
Gly Lys Leu Pro Val Pro Trp Pro Thr Leu Val Thr Thr Phe Gly Tyr
        590                 595                 600 ggc ctg cag tgc ttc gcc cgc tac ccc gac cac atg aag cag cac gac     1878
Gly Leu Gln Cys Phe Ala Arg Tyr Pro Asp His Met Lys Gln His Asp
    605                 610                 615 ttc ttc aag tcc gcc atg ccc gaa ggc tac gtc cag gag cgc acc atc     1926
Phe Phe Lys Ser Ala Met Pro Glu Gly Tyr Val Gln Glu Arg Thr Ile
620                 625                 630 ttc ttc aag gac gac ggc aac tac aag acc cgc gcc gag gtg aag ttc     1974
Phe Phe Lys Asp Asp Gly Asn Tyr Lys Thr Arg Ala Glu Val Lys Phe
        635                 640                 645 gag ggc gac acc ctg gtg aac cgc atc gag ctg aag ggc atc gac ttc     2022
Glu Gly Asp Thr Leu Val Asn Arg Ile Glu Leu Lys Gly Ile Asp Phe
650                 655                 660                 665 aag gag gac ggc aac atc ctg ggg cac aag ctg gag tac aac tac aac     2070
Lys Glu Asp Gly Asn Ile Leu Gly His Lys Leu Glu Tyr Asn Tyr Asn
                670                 675                 680
```

| | | | | | | | | | | | | | | | | |
|---|---|---|---|---|---|---|---|---|---|---|---|---|---|---|---|---|
|agc|cac|aac|gtc|tat|atc|atg|gcc|gac|aag|cag|aag|aac|ggc|atc|aag|2118|
|Ser|His|Asn|Val|Tyr|Ile|Met|Ala|Asp|Lys|Gln|Lys|Asn|Gly|Ile|Lys| |
| | | |685| | | |690| | | | |695| | | | |

| | | | | | | | | | | | | | | | | |
|---|---|---|---|---|---|---|---|---|---|---|---|---|---|---|---|---|
|gtg|aac|ttc|aag|atc|cgc|cac|aac|atc|gag|gac|ggc|agc|gtg|cag|ctc|2166|
|Val|Asn|Phe|Lys|Ile|Arg|His|Asn|Ile|Glu|Asp|Gly|Ser|Val|Gln|Leu| |
| | | |700| | | |705| | | | |710| | | | |

| | | | | | | | | | | | | | | | | |
|---|---|---|---|---|---|---|---|---|---|---|---|---|---|---|---|---|
|gcc|gac|cac|tac|cag|cag|aac|acc|ccc|atc|ggc|gac|ggc|ccc|gtg|ctg|2214|
|Ala|Asp|His|Tyr|Gln|Gln|Asn|Thr|Pro|Ile|Gly|Asp|Gly|Pro|Val|Leu| |
| | | |715| | | |720| | | | |725| | | | |

| | | | | | | | | | | | | | | | | |
|---|---|---|---|---|---|---|---|---|---|---|---|---|---|---|---|---|
|ctg|ccc|gac|aac|cac|tac|ctg|agc|tac|cag|tcc|gcc|ctg|agc|aaa|gac|2262|
|Leu|Pro|Asp|Asn|His|Tyr|Leu|Ser|Tyr|Gln|Ser|Ala|Leu|Ser|Lys|Asp| |
|730| | | |735| | | |740| | | | |745| | | |

| | | | | | | | | | | | | | | | | |
|---|---|---|---|---|---|---|---|---|---|---|---|---|---|---|---|---|
|ccc|aac|gag|aag|cgc|gat|cac|atg|gtc|ctg|ctg|gag|ttc|gtg|acc|gcc|2310|
|Pro|Asn|Glu|Lys|Arg|Asp|His|Met|Val|Leu|Leu|Glu|Phe|Val|Thr|Ala| |
| | | | |750| | | |755| | | | |760| | | |

| | | | | | | | | | | | | |
|---|---|---|---|---|---|---|---|---|---|---|---|---|
|gcc|ggg|atc|act|ctc|ggc|atg|gac|gag|ctg|tac|aag|taa|2349|
|Ala|Gly|Ile|Thr|Leu|Gly|Met|Asp|Glu|Leu|Tyr|Lys| | |
| | | |765| | | |770| | | | | | |

```
<210> SEQ ID NO 2
<211> LENGTH: 2409
<212> TYPE: DNA
<213> ORGANISM: Artificial Sequence
<220> FEATURE:
<223> OTHER INFORMATION: Artificial sequence comprising proteins from
      the following organisms: Aequorea victoria, Escherichia coli K12,
      and Mus musculus, and contains linker sequences comprising
      restriction sites and poly-Gly
<220> FEATURE:
<221> NAME/KEY: misc_feature
<222> LOCATION: (1)..(9)
<223> OTHER INFORMATION: Linker sequence comprising a restriction site:
      AAGCTT
<220> FEATURE:
<221> NAME/KEY: exon
<222> LOCATION: (10)..(69)
<223> OTHER INFORMATION: mCFP contains the N-terminal 20 amino acids of
      neuromodulin (GAP-43), which encode a posttranslational
      palmitoylation signal sequence that targets proteins to the plasma
      membrane, organism: Mus musculus
<220> FEATURE:
<221> NAME/KEY: exon
<222> LOCATION: (70)..(786)
<223> OTHER INFORMATION: Cyan Fluorescent Protein, organism: Aequorea
      victoria
<220> FEATURE:
<221> NAME/KEY: misc_feature
<222> LOCATION: (787)..(804)
<223> OTHER INFORMATION: Linker sequence comprising: poly-Gly and a
      restriction site
<220> FEATURE:
<221> NAME/KEY: exon
<222> LOCATION: (805)..(1662)
<223> OTHER INFORMATION: Glucose-galactose binding protein, organism:
      Escherichia coli K12
<220> FEATURE:
<221> NAME/KEY: misc_feature
<222> LOCATION: (1663)..(1689)
<223> OTHER INFORMATION: Linker sequence comprising: poly-Gly and a
      restriction site: GGATCC
<220> FEATURE:
<221> NAME/KEY: exon
<222> LOCATION: (1690)..(2409)
<223> OTHER INFORMATION: Yellow Fluorescent Protein, organism: Aequorea
      victoria, and stop codon "taa"

<400> SEQUENCE: 2
```

| | | | | | | | | | | | | | | |
|---|---|---|---|---|---|---|---|---|---|---|---|---|---|---|
|aagcttacc|atg|ctg|tgc|tgt|atg|aga|aga|acc|aaa|cag|gtt|gaa|aag|aat|51|
| |Met|Leu|Cys|Cys|Met|Arg|Arg|Thr|Lys|Gln|Val|Glu|Lys|Asn| |
| |1| | |5| | | | |10| | | | | | |

| | | | | | | | | | | | | | | |
|---|---|---|---|---|---|---|---|---|---|---|---|---|---|---|
|gat|gag|gac|caa|aag|atc|atg|gtg|agc|aag|ggc|gag|gag|ctg|ttc|acc|99|
|Asp|Glu|Asp|Gln|Lys|Ile|Met|Val|Ser|Lys|Gly|Glu|Glu|Leu|Phe|Thr|

```
              15                  20                  25                  30
ggg gtg gtg ccc atc ctg gtc gag ctg gac ggc gac gta aac ggc cac         147
Gly Val Val Pro Ile Leu Val Glu Leu Asp Gly Asp Val Asn Gly His
                         35                  40                  45 aag ttc agc gtg tcc ggc gag ggc gag ggc gat gcc acc tac ggc aag         195
Lys Phe Ser Val Ser Gly Glu Gly Glu Gly Asp Ala Thr Tyr Gly Lys
                 50                  55                  60 ctg acc ctg aag ttc atc tgc acc acc ggc aag ctg ccc gtg ccc tgg         243
Leu Thr Leu Lys Phe Ile Cys Thr Thr Gly Lys Leu Pro Val Pro Trp
             65                  70                  75 ccc acc ctc gtg acc acc ctg acc tgg ggc gtg cag tgc ttc agc cgc         291
Pro Thr Leu Val Thr Thr Leu Thr Trp Gly Val Gln Cys Phe Ser Arg
         80                  85                  90 tac ccc gac cac atg aag cag cac gac ttc ttc aag tcc gcc atg ccc         339
Tyr Pro Asp His Met Lys Gln His Asp Phe Phe Lys Ser Ala Met Pro
 95                 100                 105                 110 gaa ggc tac gtc cag gag cgc acc atc ttc ttc aag gac gac ggc aac         387
Glu Gly Tyr Val Gln Glu Arg Thr Ile Phe Phe Lys Asp Asp Gly Asn
                        115                 120                 125 tac aag acc cgc gcc gag gtg aag ttc gag ggc gac acc ctg gtg aac         435
Tyr Lys Thr Arg Ala Glu Val Lys Phe Glu Gly Asp Thr Leu Val Asn
                130                 135                 140 cgc atc gag ctg aag ggc atc gac ttc aag gag gac ggc aac atc ctg         483
Arg Ile Glu Leu Lys Gly Ile Asp Phe Lys Glu Asp Gly Asn Ile Leu
            145                 150                 155 ggg cac aag ctg gag tac aac tac atc agc cac aac gtc tat atc acc         531
Gly His Lys Leu Glu Tyr Asn Tyr Ile Ser His Asn Val Tyr Ile Thr
        160                 165                 170 gcc gac aag cag aag aac ggc atc aag gcc aac ttc aag atc cgc cac         579
Ala Asp Lys Gln Lys Asn Gly Ile Lys Ala Asn Phe Lys Ile Arg His
175                 180                 185                 190 aac atc gag gac ggc agc gtg cag ctc gcc gac cac tac cag cag aac         627
Asn Ile Glu Asp Gly Ser Val Gln Leu Ala Asp His Tyr Gln Gln Asn
                        195                 200                 205 acc ccc atc ggc gac ggc ccc gtg ctg ctg ccc gac aac cac tac ctg         675
Thr Pro Ile Gly Asp Gly Pro Val Leu Leu Pro Asp Asn His Tyr Leu
                210                 215                 220 agc acc cag tcc gcc ctg agc aaa gac ccc aac gag aag cgc gat cac         723
Ser Thr Gln Ser Ala Leu Ser Lys Asp Pro Asn Glu Lys Arg Asp His
            225                 230                 235 atg gtc ctg ctg gag ttc gtg acc gcc gcc ggg atc act ctc ggc atg         771
Met Val Leu Leu Glu Phe Val Thr Ala Ala Gly Ile Thr Leu Gly Met
        240                 245                 250 gac gag ctg tac aag ggaatccgcg gtggtggt gct gat act cgc att ggt        822
Asp Glu Leu Tyr Lys                      Ala Asp Thr Arg Ile Gly
255                                              260                 265 gta aca atc tat aag tac gac gat aac ttt atg tct gta gtg cgc aag         870
Val Thr Ile Tyr Lys Tyr Asp Asp Asn Phe Met Ser Val Val Arg Lys
                270                 275                 280 gct att gag caa gat gcg aaa gcc gcg cca gat gtt cag ctg ctg atg         918
Ala Ile Glu Gln Asp Ala Lys Ala Ala Pro Asp Val Gln Leu Leu Met
            285                 290                 295 aat gat tct cag aat gac cag tcc aag cag aac gat cag atc gac gta         966
Asn Asp Ser Gln Asn Asp Gln Ser Lys Gln Asn Asp Gln Ile Asp Val
        300                 305                 310 ttg ctg gcg aaa ggg gtg aag gca ctg gca atc aac ctg gtt gac ccg        1014
Leu Leu Ala Lys Gly Val Lys Ala Leu Ala Ile Asn Leu Val Asp Pro
    315                 320                 325 gca gct gcg ggt acg gtg att gag aaa gcg cgt ggg caa aac gtg ccg        1062
Ala Ala Ala Gly Thr Val Ile Glu Lys Ala Arg Gly Gln Asn Val Pro
```

```
                   330              335              340              345
gtg gtt ttc ttc aac aaa gaa ccg tct cgt aag gcg ctg gat agc tac    1110
Val Val Phe Phe Asn Lys Glu Pro Ser Arg Lys Ala Leu Asp Ser Tyr
                    350              355              360 gac aaa gcc tac tac gtt ggc act gac tcc aaa gag tcc ggc att att    1158
Asp Lys Ala Tyr Tyr Val Gly Thr Asp Ser Lys Glu Ser Gly Ile Ile
            365              370              375 caa ggc gat ttg att gct aaa cac tgg gcg gcg aat cag ggt tgg gat    1206
Gln Gly Asp Leu Ile Ala Lys His Trp Ala Ala Asn Gln Gly Trp Asp
        380              385              390 ctg aac aaa gac ggt cag att cag ttc gta ctg ctg aaa ggt gaa ccg    1254
Leu Asn Lys Asp Gly Gln Ile Gln Phe Val Leu Leu Lys Gly Glu Pro
    395              400              405 ggc cat ccg gat gca gaa gca cgt acc act tac gtg att aaa gaa ttg    1302
Gly His Pro Asp Ala Glu Ala Arg Thr Thr Tyr Val Ile Lys Glu Leu
410              415              420              425 aac gat aaa ggc atc aaa act gaa cag tta cag tta gat acc gca atg    1350
Asn Asp Lys Gly Ile Lys Thr Glu Gln Leu Gln Leu Asp Thr Ala Met
                430              435              440 tgg gac acc gct cag gcg aaa gat aag atg gac gcc tgg ctg tct ggc    1398
Trp Asp Thr Ala Gln Ala Lys Asp Lys Met Asp Ala Trp Leu Ser Gly
            445              450              455 ccg aac gcc aac aaa atc gaa gtg gtt atc gcc aac aac gat gcg atg    1446
Pro Asn Ala Asn Lys Ile Glu Val Val Ile Ala Asn Asn Asp Ala Met
        460              465              470 gca atg ggc gcg gtt gaa gcg ctg aaa gca cac aac aag tcc agc att    1494
Ala Met Gly Ala Val Glu Ala Leu Lys Ala His Asn Lys Ser Ser Ile
    475              480              485 ccg gtg ttt ggc gtc gat gcg ctg cca gaa gcg ctg gcg ctg gtg aaa    1542
Pro Val Phe Gly Val Asp Ala Leu Pro Glu Ala Leu Ala Leu Val Lys
490              495              500              505 tcc ggt gca ctg gcg ggc acc gta ctg aac gat gct aac aac cag gcg    1590
Ser Gly Ala Leu Ala Gly Thr Val Leu Asn Asp Ala Asn Asn Gln Ala
                510              515              520 aaa gcg acc ttt gat ctg gcg aaa aac ctg gcc gat ggt aaa ggt gcg    1638
Lys Ala Thr Phe Asp Leu Ala Lys Asn Leu Ala Asp Gly Lys Gly Ala
            525              530              535 gct gat ggc acc aac tgg aaa atc ggtggtggtg cggatccacc ggtcgcc atg   1692
Ala Asp Gly Thr Asn Trp Lys Ile                                Met
        540              545 gtg agc aag ggc gag gag ctg ttc acc ggg gtg gtg ccc atc ctg gtc    1740
Val Ser Lys Gly Glu Glu Leu Phe Thr Gly Val Val Pro Ile Leu Val
    550              555              560 gag ctg gac ggc gac gta aac ggc cac aag ttc agc gtg tcc ggc gag    1788
Glu Leu Asp Gly Asp Val Asn Gly His Lys Phe Ser Val Ser Gly Glu
565              570              575 ggc gag ggc gat gcc acc tac ggc aag ctg acc ctg aag ttc atc tgc    1836
Gly Glu Gly Asp Ala Thr Tyr Gly Lys Leu Thr Leu Lys Phe Ile Cys
                580              585              590 acc acc ggc aag ctg ccc gtg ccc tgg ccc acc ctc gtg acc acc ttc    1884
Thr Thr Gly Lys Leu Pro Val Pro Trp Pro Thr Leu Val Thr Thr Phe
595              600              605              610 ggc tac ggc ctg cag tgc ttc gcc cgc tac ccc gac cac atg aag cag    1932
Gly Tyr Gly Leu Gln Cys Phe Ala Arg Tyr Pro Asp His Met Lys Gln
            615              620              625 cac gac ttc ttc aag tcc gcc atg ccc gaa ggc tac gtc cag gag cgc    1980
His Asp Phe Phe Lys Ser Ala Met Pro Glu Gly Tyr Val Gln Glu Arg
        630              635              640 acc atc ttc ttc aag gac gac ggc aac tac aag acc cgc gcc gag gtg    2028
Thr Ile Phe Phe Lys Asp Asp Gly Asn Tyr Lys Thr Arg Ala Glu Val
```

-continued

| | | | | | | | | | | | | |
|---|---|---|---|---|---|---|---|---|---|---|---|---|
| | | 645 | | | | 650 | | | | 655 | | |
| aag | ttc | gag | ggc | gac | acc | ctg | gtg | aac | cgc | atc | gag | ctg | aag | ggc | atc | 2076 |
| Lys | Phe | Glu | Gly | Asp | Thr | Leu | Val | Asn | Arg | Ile | Glu | Leu | Lys | Gly | Ile |
| | 660 | | | | | 665 | | | | | 670 | | | | |
| gac | ttc | aag | gag | gac | ggc | aac | atc | ctg | ggg | cac | aag | ctg | gag | tac | aac | 2124 |
| Asp | Phe | Lys | Glu | Asp | Gly | Asn | Ile | Leu | Gly | His | Lys | Leu | Glu | Tyr | Asn |
| 675 | | | | | 680 | | | | | 685 | | | | | 690 |
| tac | aac | agc | cac | aac | gtc | tat | atc | atg | gcc | gac | aag | cag | aag | aac | ggc | 2172 |
| Tyr | Asn | Ser | His | Asn | Val | Tyr | Ile | Met | Ala | Asp | Lys | Gln | Lys | Asn | Gly |
| | | | 695 | | | | | 700 | | | | | 705 | | |
| atc | aag | gtg | aac | ttc | aag | atc | cgc | cac | aac | atc | gag | gac | ggc | agc | gtg | 2220 |
| Ile | Lys | Val | Asn | Phe | Lys | Ile | Arg | His | Asn | Ile | Glu | Asp | Gly | Ser | Val |
| | | | 710 | | | | | 715 | | | | | 720 | | |
| cag | ctc | gcc | gac | cac | tac | cag | cag | aac | acc | ccc | atc | ggc | gac | ggc | ccc | 2268 |
| Gln | Leu | Ala | Asp | His | Tyr | Gln | Gln | Asn | Thr | Pro | Ile | Gly | Asp | Gly | Pro |
| | | 725 | | | | | 730 | | | | | 735 | | | |
| gtg | ctg | ctg | ccc | gac | aac | cac | tac | ctg | agc | tac | cag | tcc | gcc | ctg | agc | 2316 |
| Val | Leu | Leu | Pro | Asp | Asn | His | Tyr | Leu | Ser | Tyr | Gln | Ser | Ala | Leu | Ser |
| | 740 | | | | | 745 | | | | | 750 | | | | |
| aaa | gac | ccc | aac | gag | aag | cgc | gat | cac | atg | gtc | ctg | ctg | gag | ttc | gtg | 2364 |
| Lys | Asp | Pro | Asn | Glu | Lys | Arg | Asp | His | Met | Val | Leu | Leu | Glu | Phe | Val |
| 755 | | | | | 760 | | | | | 765 | | | | | 770 |
| acc | gcc | gcc | ggg | atc | act | ctc | ggc | atg | gac | gag | ctg | tac | aag | taa | | 2409 |
| Thr | Ala | Ala | Gly | Ile | Thr | Leu | Gly | Met | Asp | Glu | Leu | Tyr | Lys |
| | | | | 775 | | | | | 780 | | | | | | |